(12) United States Patent
Dwyer et al.

(10) Patent No.: US 9,579,396 B2
(45) Date of Patent: Feb. 28, 2017

(54) FINITE FULLY ADDRESSABLE NUCLEIC ACID NANOSTRUCTURES AS NANOCARRIERS FOR DELIVERY OF PHARMACEUTICALS

(75) Inventors: Chris Dwyer, Durham, NC (US); Hong Zhong, Huntington, WV (US); Michael Norton, Huntington, WV (US); Steven Armentrout, Reston, VA (US)

(73) Assignee: PARABON NANOLABS, INC., Reston, VA (US)

( * ) Notice: Subject to any disclaimer, the term of this patent is extended or adjusted under 35 U.S.C. 154(b) by 0 days.

(21) Appl. No.: 14/115,600

(22) PCT Filed: May 4, 2012

(86) PCT No.: PCT/US2012/036617
§ 371 (c)(1),
(2), (4) Date: May 8, 2015

(87) PCT Pub. No.: WO2012/151537
PCT Pub. Date: Nov. 8, 2012

(65) Prior Publication Data
US 2015/0320883 A1 Nov. 12, 2015

Related U.S. Application Data

(60) Provisional application No. 61/482,448, filed on May 4, 2011.

(51) Int. Cl.
| | |
|---|---|
| *A61K 48/00* | (2006.01) |
| *A61K 47/48* | (2006.01) |
| *A61K 38/16* | (2006.01) |
| *A61K 31/7052* | (2006.01) |
| *A61K 31/337* | (2006.01) |
| *A61K 39/385* | (2006.01) |
| *A61K 39/00* | (2006.01) |
| *A61K 31/7088* | (2006.01) |
| *A61K 38/00* | (2006.01) |

(52) U.S. Cl.
CPC ...... *A61K 47/48884* (2013.01); *A61K 31/337* (2013.01); *A61K 31/7052* (2013.01); *A61K 38/164* (2013.01); *A61K 39/385* (2013.01); *A61K 47/48092* (2013.01); *A61K 31/7088* (2013.01); *A61K 38/00* (2013.01); *A61K 48/00* (2013.01); *A61K 2039/6025* (2013.01); *Y10T 428/2982* (2015.01)

(58) Field of Classification Search
None
See application file for complete search history.

(56) References Cited

FOREIGN PATENT DOCUMENTS

WO  WO 2010/040091 A1 * 4/2010 ........... A61K 31/711

OTHER PUBLICATIONS

Lee et al. Advanced Drug Delivery Reviews (2010), vol. 62, pp. 606-616.*
Gregory A. Petsko, Dagmar Ringe, "Protein Structure and Function," Flexibility and Function 2-2, p. 55, 2004, U.S.
David Harvey, "Analytical Chemistry 2.0," 3.4 Selecting an Analytical Method, McGraw-Hill, 1999, U.S.
Chhabra, Rahul, et al., "DNA Self-assembly for Nanomedicine," Advanced Drug Delivery Reviews 62.6, pp. 617-625, 2010, U.S.

* cited by examiner

*Primary Examiner* — Patrick Lewis
(74) *Attorney, Agent, or Firm* — Scott D Balderston

(57) ABSTRACT

The present invention provides nanostructures that are particularly well suited for delivery of bioactive agents to organs, tissues, and cells of interest in vivo, and for diagnostic purposes. In exemplary embodiments, the nanostructures are complexes of DNA strands having fully defined nucleotide sequences that hybridize to each other in such a way as to provide a pre-designed three dimensional structure with binding sites for targeting molecules and bioactive agents. The nanostructures are of a pre-designed finite length and have a pre-defined three dimensional structure.

26 Claims, 12 Drawing Sheets

The Structure of the PNL24 Complex

FINITE FULLY ADDRESSABLE NUCLEIC ACID NANOSTRUCTURES AS NANOCARRIERS FOR DELIVERY OF PHARMACEUTICALS

CROSS-REFERENCE TO RELATED APPLICATIONS

The present application relies on the disclosure of, and claims the benefit of the filing date of, U.S. provisional patent application No. 61/482,448, filed 4 May 2011.

BACKGROUND OF THE INVENTION

Field of the Invention

The present invention relates to the fields of molecular biology and medicine. More specifically, in exemplary embodiments the invention relates to fully engineered nucleic acid superstructures that are engineered to bind and deliver bioactive molecules to target cells or target bioactive molecules to effect medical or clinical treatment.

Description of Related Art

Nucleic acid scaffolds having defined structures are known in the art. For example, U.S. Pat. No. 5,561,043 to Cantor et al. discloses self-assembling nucleic acid aggregates that comprise (1) a first construct comprising a plurality of first single-stranded nucleic acids bound to a first coupling agent forming a first multimer; (2) a second construct comprising a plurality of second single-stranded nucleic acids bound to a second coupling agent forming a second multimer, at least one of the second single-stranded nucleic acids hybridizing with a complementary sequence of one of the first single-stranded nucleic acids; and (3) a plurality of third single-stranded nucleic acids, each of the third single-stranded nucleic acids being attached to a functional group, and each of the third single-stranded nucleic acids hybridizing with a complementary sequence of a single-stranded nucleic acid attached to the aggregate, wherein the first coupling agent and the second coupling agent each include a protein, a 5'-amino-containing oligonucleotide, a 5'-thiol-containing oligonucleotide, a polyamidoamine, or a divalent linker.

U.S. Pat. No. 6,255,469 to Seeman et al. discloses a periodic polynucleic acid structure comprising a lattice of adjacent coplanar repeating units, each repeating unit comprising at least two antiparallel nucleic acid multi-crossover molecules, each of the at least two antiparallel nucleic acid multi-crossover molecules comprising two or more adjacent double helical domains, at least two of the two or more adjacent double helical domains having a first and second cohesive ends, each of the adjacent double helical domains having helix axes in parallel and being connected to adjacent double helical domains at two or more crossover sites, with each antiparallel nucleic acid multi-crossover molecules being connected to an adjacent antiparallel nucleic acid multi-crossover molecule by complementary cohesive ends, thereby forming an extended double helical domain between a first double helical domain of an antiparallel nucleic acid multi-crossover molecule and a second double helical domain of an adjacent antiparallel nucleic acid multi-crossover molecule, wherein a second double helical domain of the antiparallel nucleic acid multi-crossover molecule is not colinear and connectable with a first double helical domain of the adjacent antiparallel nucleic acid crossover molecule to form an extended double helical domain, and wherein each repeating unit is connected to an adjacent repeating unit in the same plane by complementary cohesive ends to form at least one extended double helical domain between adjacent repeating units in the same plane. In addition, methods of making such structures are disclosed. Embodiments of the invention include those in which the structure can include chemically or biologically active molecules.

U.S. Pat. No. 6,814,964 to Virtanen et al. discloses a supramolecule comprising (1) a first supramolecular component having a binding effector molecule covalently joined to at least one first nucleic acid, (2) a second supramolecular component having a therapeutic effector molecule covalently joined to at least one second nucleic acid, wherein at least a portion of the at least one first nucleic acid is hybridized to at least a portion of the at least one second nucleic acid, and wherein the binding effector molecule and the therapeutic effector molecule are selected from the group consisting of proteins, polypeptides, lipids, and sugars. The patent also discloses that the supramolecule can be provided in the form of a pharmaceutical. The patent disclosure is focused on use of such molecules in methods of hydrolyzing viruses.

U.S. Pat. No. 7,223,544 and U.S. Pat. No. 7,799,903 to Luo et al. disclose a method of making a three-dimensional nucleic acid structure formed with a trimer, the method comprising combining a first, a second, and a third polynucleotide in a solution, wherein at least a portion of the first polynucleotide is complementary to at least a portion of the second polynucleotide, wherein at least a portion of the first polynucleotide is complementary to at least a portion of the third polynucleotide; and wherein at least a portion of the second polynucleotide is complementary to at least a portion of the third polynucleotide; and maintaining the solution at conditions effective for the first, second, and third polynucleotides to associate together to form a trimer, wherein each polynucleotide comprises a sticky end, and wherein the sequence of each sticky end is non-complementary. These documents further disclose that the invention described in them provides a solution for a need in the art for branched (Y-shaped) DNA molecules with precisely controlled sizes, which can be incorporated into dendrimer-like DNA (DL-DNA). The DL-DNA is disclosed as useful for, among other things, controlled drug delivery.

U.S. Pat. No. 7,598,363 to Seeman et al. discloses a polynucleic acid structure comprising a polygonal unit whose edges are parallel helices of connected nucleic acid multi-crossover domains along their helix axes, each of the edges having at least one free end with two parallel helices, wherein each of the two parallel helices at one free end of each of the edges terminate in a cohesive end to provide a double cohesive end on the one free end. The patent discloses that the invention described in the document differs from the prior art in that the structures include DNA double crossover (DX) molecules, rather than conventional DNA double helices. Further, the patent discloses that the structures are useful for, among other things, immobilizing enzymes and other catalysts.

U.S. Pat. No. 7,622,567 to Seeman et al. discloses a two dimensional polynucleic acid array of polygonal units linked together by complementary double cohesive ends, comprising a plurality of polygonal units, wherein each of the polygonal units has, as edges, parallel helices of connected nucleic acid multi-crossover domains along their helix axes; each of at least two of the edges of each of the polygonal units has ends with two parallel double helices; each of the two parallel double helices terminate in a cohesive end to provide a double cohesive end at each end of the at least two edges, whereby the double cohesive end of one edge of a polygonal unit is cohered to a complementary double cohesive end of an adjacent polygonal unit in the array to form an extended edge linking together two adjacent polygonal units; and at least one edge, which is different from the at least two edges, of a subset of said polygonal units has at least one end which is attached to a nanoparticle or pendant molecule. The patent discloses that the invention relates to new motifs for polynucleic acid arrays, which is stiffer or more rigid than prior art bulged-junction triangles.

U.S. patent application publication number 2009/0018028 to Lindsay et al., incorporated herein in its entirety by reference, discloses self-assembling, finite nucleic acid tiling arrays, and methods for their synthesis and use. The publication discloses that the invention provides a nucleic acid tiling array comprising a plurality of nucleic acid tiles joined to one another via sticky ends, wherein each nucleic acid tile comprises one or more sticky ends, and wherein a sticky end for a given nucleic acid tile is complementary to a single sticky end of another nucleic acid tile in the nucleic acid tiling array; wherein the nucleic acid tiles are present at predetermined positions within the nucleic acid tiling array as a result of programmed base pairing between the sticky ends of the nucleic acid tiles.

While numerous technologies and nucleic acid nanostructures have been developed to date in the art, none of those nanostructures has been disclosed that has a pre-selected, finite size and that is completely engineered to include specific binding sites for one or more substances that can function in targeting of the nucleic acid nanostructure to a desired target, and delivery of the nanostructure and the attached substance(s) to the target, where target refers to any bioactive molecule, bioactive complex, or biological cell.

SUMMARY OF THE INVENTION

The present invention addresses needs in the art by providing nanostructures, and their core structures, built from one or more polymer types, preferably where one or more, or each, type differs by its length and sequence of monomeric subunits. The linear sequence of monomeric subunits comprising each polymer type is deliberately assigned, i.e., engineered, to allow the polymer to bond in specific, pre-defined arrangements with other polymers, resulting in a nanostructure having the three-dimensional shape and finite size desired by its designer. In particular, its primary, secondary, and tertiary structure, its size, and the relative positions of the monomers in the polymers are all determined by design. Moreover, it is of a fixed and finite size (typically between 2 nm and 1,000 nm) specified by its designer. This is in contrast to periodic nanostructures (e.g., the arrays of U.S. Pat. No. 7,622,567), the size of which is arbitrary, depending on the finite availability of material and the shearing forces that prevent such structures from growing to an infinite size. The nanostructures of the present invention are engineered using computer software and known physical and chemical properties of polymers and the monomers from which they are made. While any type of polymer can be used in forming the nanostructures of the invention, preferred polymers are biologically tolerable and, preferably, biodegradable or excretable. While all types of polymers are contemplated by the present invention, exemplary polymers for use in fabrication of the nanostructures are nucleic acids and polypeptides.

In one exemplary aspect, the invention provides nucleic acid nanostructures, their core structures, and functionalized core structures, fabricated from one or multiple nucleic acid strands, each of which has a primary nucleotide sequence that is engineered in conjunction with the sequences of the other nucleic acid strands of the nanostructure, if present. The collection of nucleic acid strands is engineered such that, when combined under conditions that permit annealing of the nucleic acid strands to themselves or, if present to other nucleic acid strands, they form into multiple, identical copies of a specific core structure subunit or a full core structure, the finite size and shape of which are pre-determined by design. In the case where core structure subunits are created, these then can be combined to form multiple, identical core structures of the nanostructures, the finite size and shape of which are pre-determined by design. The engineered nanostructures of the invention have one or more binding sites for substances of interest at precisely defined positions in the core structure, which can be engineered by a designer at design time, on or within the nanostructures. The relative location of and, if multiple positions are used, the distances between the positions is engineered by design at design time. For example, the current invention allows a designer to designate three binding sites that form an equilateral triangle on the surface of a nanostructure where the distance between any two is exactly 5 nm. This is in contrast to other nanotechnologies, such as liposomes, where the location of functional binding sites cannot be specified at design time; rather, they are determined arbitrarily at assembly time by the chemical forces that govern their formation, which are statistical in nature.

In another exemplary aspect, the invention provides polypeptide nanostructures fabricated from one or multiple polypeptides, their core structures, and functionalized core structures. Each of the polypeptides that makes up the core structure has a primary amino acid sequence that is engineered in conjunction with the other polypeptide strands of the core structure, if present. The collection of polypeptides is engineered such that, when combined under conditions that permit proper folding of each polypeptide and proper interaction among the various different polypeptides, if present, they form into multiple, identical copies of a specific core structure subunit or a full core structure, the finite size and shape of which are pre-determined by design. In the case where core structure subunits are created, these then can be combined to form multiple, identical core structures, which have a finite size and a shape that are pre-determined by design. The engineered nanostructures of the invention have one or more binding sites for substances of interest at precisely defined positions in the core structure, which can be engineered by a designer at design time, on or within the nanostructures. The relative location of and, if multiple positions are used, the distances between the positions is engineered by design at design time. For example, the current invention allows a designer to designate three binding sites that form an equilateral triangle on the surface of a nanostructure where the distance between any two is exactly 5 nm. This is in contrast to other nanotechnologies, such as liposomes, where the location of functional binding sites cannot be specified at design time; rather, they are determined arbitrarily at assembly time by the chemical forces that govern their formation, which are statistical in nature.

The nanostructures of the present invention differ from structures known in the art. For example, the lattices reported by Park et al. (Park, S. H., C. Pistol, S. J. Ahn, J. H. Reif, A. R. Lebeck, C. Dwyer, T. H. Labean, "Finite-size, Fully-Addressable DNA Tile Lattices Formed by Hierarchical Assembly Procedures", Angewandte Chemie, vol. 45, pp. 735-739, January 2006) are similar to a subset of the nanostructures described herein; however, the current invention introduces nanostructure functionalizations for a variety of pharmaceutical and diagnostic purposes, including but not limited to cell targeting, pharmaceutical payload delivery, cell sensitization to specific payloads and imaging enhancement. Likewise, the DNA origami structures reported by Rothemund (Rothemund, P. W. K., "Folding DNA to create nanoscale shapes and patterns", Nature, vol. 440, pp. 297-302, 2006) are similar to the DNA origami nanostructures of certain embodiments of the present invention. However, the current nanostructures allow for DNA origami functionalized for delivery of pharmaceuticals.

The half-life of a nanoparticle, such as the present nanostructures, in vivo is relevant to the medical applications of the nanoparticle. To date, there are no reports of nanostructures with pre-determined structure and finite size that have been tested in a mammalian animal and shown to have a significant half-life. In Example 3, below, exemplary DNA nanostructures of the present invention showed a 2.7 hour tissue half-life in vivo in mice. In comparison, the half-life of previously tested plasmid DNA in vivo was only about 10 minutes. The present invention thus provides, at least with respect to nucleic acid nanostructures, an unexpectedly superior in vivo half-life, which permits real-world use of the structures for therapeutic, imaging, and diagnostic applications.

As one of the differentiators that differentiate the current invention from the prior art, the finite size of the nanostructures in this invention, and the ability to engineer the nanostructures to have a pre-determined finite size, plays an important role in their medical applications. For example, nanoparticles smaller than 30 nm or larger than 200 nm tend to be cleared from the plasma circulation much more rapidly than nanoparticles with a size between 30 nm and 200 nm. As such, for medical applications, it is preferred that the nanostructures have a size within this range. Exemplary sizes include, but are not limited to, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, and 200 nm. Of course, the ordinary artisan will immediately recognize that all sizes within this range are contemplated as part of the invention by the inventors and by the present invention and document, and that all of the sizes falling within the range are not specifically listed herein solely to conserve space. Further, it is understood that all ranges defined by all size points falling within this range are contemplated as part of the invention by the inventors and by the present invention and document, and that each range is not specifically listed herein solely to conserve space in this document and to avoid disclosure of what is immediately evident to the ordinary artisan. Thus, for example, it is to be understood that nanostructures according to the present invention can have a size of 58 nm or can have a size range of from 36 nm to 172 nm While the nanostructures of the invention have advantageous use in vivo, their utility is not so limited. More specifically, the nanostructures also have real-world utility in in vitro for the enrichment of specific cell type(s). For example, the nanostructures can be covalently attached to the stationary phase of a column and cell samples with various cell types can be run through the column. Cells of interest are bound in the column and, therefore, enriched.

For many in vitro applications, the preferred size range might be the same as for in vivo applications. In both in vivo and in vitro applications, the size of the nanostructure can be any size, or any size range, between 2 nm and 1,000 nm, such as but not limited to, 10 nm, 20 nm, 25 nm, 225 nm, 250 nm, 300 nm, 350 nm, 400 nm, 450 nm, 500 nm, 550 nm, 600 nm, 650 nm, 700 nm, 750 nm, 800 nm, 850 nm, 900 nm, and 950 nm. In accordance with the disclosure, above, the ordinary artisan will immediately understand that all specific sizes and all possible ranges encompassed by those sizes are contemplated by the inventors as part of the present invention without the need to specifically list each and every size and range. Each size and range is not specifically listed solely to conserve space in this document and to avoid disclosure of what is immediately evident to the ordinary artisan.

The techniques used to functionalize specific nanostructures enabled under this invention that, at least in part, differentiate the current invention from the prior art vary by the type of bonding employed, relative distance between two or more functional moieties, the overall spatial arrangement of functional components, and the strategy for ligand selection. The techniques are thus not particularly limited and the skilled artisan can select from any of the available techniques that are suitable for the intended application at the time of practicing the invention. In general, any technique that is suitable for bonding, either directly or indirectly, a functional moiety to a polymer that is part of a nanostructure can be used in accordance with the present invention. Numerous suitable functionalizing reagents, linkers, and the like are known in the art, and the practitioner may select an appropriate means for bonding the functional moiety to an polymer of the nanostructure as a matter of routine course. For example, one use of the current technology is to transfect into cells functional genetic material, such as small interfering RNA (siRNA). For a particular siRNA to affect a cell's RNA interference pathway, it must enter the cell cytosol and be present at some point in time in a free state, unbound to any nano-carrier. As an example of a functional linker used under the current invention, a Sulfo-LC-SPDP crosslinker can be used to conjugate a designated DNA strand within a particular nanostructure with a chosen siRNA in a manner that ensures their cleavage in the low-pH environment of the cytosol, thus delivering the siRNA cargo to its target environment. The FRET signal of a specific FRET dye pair is very sensitive to the variation of distance between the two dyes. FRET dyes can be designed and assembled into nanostructures in this invention with optimal distance for different applications. For example, the change of FRET signal in the nanostructures can be used to monitor the intracellular degradation of the nano structures. The more nanostructures are degraded, the energy transfer is less effective because the degradation is associated with the dissociation of the FRET dye pair.

The distance between two functional moieties or groups can also affect the binding of the nanostructures in this invention to their targets. For example, the extracellular domain of $\alpha V\beta 3$ integrin is about 10 nm×10 nm×8 nm in three dimensions. In an RGD peptide-functionalized nanostructure, if the distance between two RGD peptides is shorter than 8 nm, it is impossible for the two RGD peptides to bind with two $\alpha V\beta 3$ integrin molecules on the surface of the same cell simultaneously, which will result in lower affinity to a target cell.

The precise spatial arrangement of functional moieties can also be an advantageous design facet enabled by the current invention. For example, for the creation of nanostructure-based vaccines, a chosen antigen can be presented on the surface of a nanostructure under the current invention in the type of highly ordered, pentameric antigen presentation patterns shown to elicit the most potent, rapid, and efficient immune response. A spatial arrangement with repeated antigens or haptens 5-10 nm away from each other can maximize the immunogenicity of the antigens or haptens. A nanostructure-based vaccine means a nanostructure of this invention designed as vaccine against a target of interest.

Another feature made possible by the invention is a particular strategy for selecting and deploying binding ligands for a particular target molecule, namely, a strategy of using pre-defined multiple, low affinity binding elements to achieve highly specific targeting of particular cell types. Nearly all targeted drug delivery nanostructures employ targeting ligands that, individually, have high individual binding affinity (Kd<100 nM) for a designated target receptor or other species present on the surface of the target cell type. Without loss of generality, the term "receptors" is used hereafter, but the discussion applies to other targetable species on the surface of a cell. High affinity ligands tend to bind to their targeted receptors when they first make contact with them. Unfortunately, with few exceptions, cell binding receptors are not unique to a specific cell line. Thus, high affinity binding ligands can cause binding of a targeted nanostructure to non-target cell types. While receptor types are rarely, if ever, unique to specific cell lines, certain classes of cells, e.g., cancer cells, are distinguishable from normal cells by their overexpression of certain types of cell surface receptors. Targeting receptors that can be bound by molecular recognition species, overexpressed or otherwise, with high affinity binding ligands can lead to delivery of nanostructures to non-targeted cells because only one strong binding event is required for attachment. It is therefore desirable to avoid such non-specific binding so as minimize effects on off-target cells. The alternative, using single, low affinity targeting ligands is not satisfactory because such weak interactions can seldom lead to binding to the targeted receptor or cell surface feature sufficiently to initiate further cellular processing leading to entry of the targeted nanostructure into the cell or induce desirable biological process, and, therefore, the nanostructure is subject to being cleared by the liver and/or spleen without inducing its desired effect on the targeted cells. The solution provided in embodiments of the present invention is to arrange for multiple, low affinity interactions, as can be employed in the systems described here. Because the current invention enables multiple targeting ligands to be arranged in close and exact proximity, a collection of lower affinity targeting ligands can be used to collectively induce high affinity binding on targeted cells that have a large number of surface bound species that can be targeted for binding, including but not limited to particular binding receptors which are overexpressed. Yet, because multiple binding events are required for such a targeted nanostructure to bind to its targeted cell, the construct is less likely to bind to normal cells that lack multiple targeted sites, including, for example, overexpressed target receptors. Moreover, because of the predetermined structure of the invention, the number of ligands that may possibly take part in the interactions with a specific target cell is well controlled. Therefore, the affinity of the nanostructures in this invention can be precisely controlled, which is unlike, or may be contrasted with, the multiple ligands attached to the flexible arms in branched molecules with random numbers of ligands binding to targets during a binding event (e.g., dendrimer or micelle structures; Carlson, C., Mowery, P., Owen, R., Dykhuizen, E. and Kiessling, L., "Selective Tumor Cell Targeting Using Low-Affinity, Multivalent Interactions", ACS Chem. Biol., 2007, 2 (2), pp 119-127.). In this way, ultra-high targeting specificity can be achieved with minimal off-target effects with the current invention.

The nanostructures of the invention have numerous in vitro, in vivo, and ex vivo uses, as those of skill in the art will immediately recognize. Exemplary embodiments detailed herein are directed to in vivo use as delivery vehicles for one or more biologically active substances, such as pharmaceuticals, biologics, and sensitizers (e.g., particular types of siRNA have been shown to reduce the resistance of particular types of cancer cell to particular therapeutic agents, "sensitizing" the cells for treatment). The invention thus provides methods for treating a subject in need of such treating. The method of treating generally includes administering to a subject a nanostructure according to the invention in an amount sufficient to result in delivery of the nanostructure to a desired site in the body of the subject. The methods for treating can be thought of as methods for treating the subject, methods for treating a cell, tissue, or organ, or methods for treating a disease or disorder. The methods can also be considered in terms of use of the nanostructures as biologically active agents, use in methods for treating, and use in making a substance for use in treating.

One aspect of the invention relates to in vitro use of the nanostructures, namely, the transfection of genetic material into cells. This aspect of the invention relates in embodiments to reagents for effecting transfection. This aspect of the invention lends itself to modifying cell function (e.g., via delivery of siRNA) or studying potential effects of gene therapy treatments. The methods are similar for constructing specific nanostructures for pharmaceutical uses. One difference is the preparation of "blank" nanostructures that can, with suitable protocols, serve as reagents for use in creating custom transfection compounds. The targeting aspect of the invention has been shown to be important to effective transfection. The nanostructures can selectively transfect one or more types of cells in a mixture of different types of cells, which can have many applications. For example, in vitro biological models with a combination of different cell types can be established. The nanostructures can be used to specifically transfect genetic materials to one or some of the cell types. The effects of transfection on transfected cells and other cells in a complex (multiple cell type) in vitro system can be studied as a cost effective means of understanding in vivo transfection.

In yet another general aspect of the invention, a method of making a nanostructure of the invention is provided. Starting with a target design created by a nano-engineer based on a desired use, the "polymeric infrastructure" or "core structure" of a nanostructure is produced using a four-step process. First, one or more computing devices are used to design the primary linear sequence of monomers for the polymer(s) that are to make up the nanostructure. Using known chemical and physical properties of the monomers (e.g., "normal" A:T and G:C nucleotide base pairing; hydrophobic-hydrophobic amino acid interactions), the computing device(s) determines the appropriate sequences for each polymer such that collectively their interactions produce nanostructures matching the shape and size of a particular design. Next, the polymers are independently fabricated using known techniques, such as in vitro chemical or biochemical synthesis (e.g., polymerase chain reaction synthesis of nucleic acids; in vitro transcription/translation) or in vivo biological synthesis (e.g., recombinant expression of nucleic acids and/or polypeptides). Next, the polymer(s) are allowed to form intra-molecular and/or inter-molecular bonds to create a core structure subunit having the desired size and shape. In the formation step, each polymer may be allowed to fold independently of the other polymers, some polymers may be allowed to fold together in the same environment, or all polymers may be combined and allowed to fold together in the same environment. Preferably, all of the polymers are combined, denatured, then allowed to fold together, resulting in pre-determined inter- and intra-molecular bonding among all of the polymers of the core structure subunit. In embodiments, the core structure subunit is the core structure. Finally, where appropriate, multiple core structure subunits are combined under conditions that allow for specific, controlled binding of the subunits to the appropriate partners to form the nanostructure core structure. It is to be understood that the subunits can have the same general structure or different structures. The core structure makes up one aspect of the invention.

The core structure can further be functionalized by forming specific sites, areas, pockets, etc. that have suitable chemical and physical characteristics for specific binding of one or more substances of interest, such as substances that specifically bind a particular cell type and substances that have a biological effect (e.g., a cytotoxin). Functionalization can be performed during the process of formation of the polymers, after the polymers have been formed, or after the nanostructure has been formed. Functionalized core structures make up one aspect of the invention.

The invention includes kits for packaging and delivering nanostructures of the invention. In general, kits according to the invention include at least the polymers that make up the core structure of a nanostructure according to the invention, in combination with packaging materials that allow for transport of the polymers from one location to another. The polymers can be functionalized or not. In embodiments, the kit comprises a core structure of a nanostructure of the invention. The core structure can be functionalized or not. Preferably, a kit according to the invention comprises a fully-formed nanostructure of the invention, complete with one or more moieties for interaction with a target substance or for delivery of a cargo or payload to a target environment.

As discussed above, numerous nucleic acid nanostructures are known in the art. However, to the inventors' knowledge, disclosures in the prior art have not enabled the creation of nanostructures with predetermined structure and finite size having fully addressable (i.e., specifically definable) binding sites for specific substances of interest at any chosen site within the nanostructure with multi-valent, low affinity, binding effectors. Moreover, while prior disclosures of nucleic acid nanostructures include placement of three dimensional features extending from one surface of a generally planar nanostructure, no previous disclosure enables one to create a structure that has multiple copies of different biologically active features extending from both surfaces of such generally planar nanostructures. Further, while various nucleic acid nanostructures have been prepared, none have been shown to have any in vivo biological activity in mammalian animal. Indeed, until the disclosure of the present invention, the ability of nucleic acid nanostructures with pre-determined structure and finite size to be stable in mammalian animals was completely unpredictable. The surprising result that the nucleic acid nanostructures according to the present invention are not only stable in vivo, but are also capable of delivering one or more bioactive agents to a target site within the body of a subject, is a significant breakthrough in the field of nanobiology and medicine.

BRIEF DESCRIPTION OF THE DRAWINGS

The accompanying drawings, which are incorporated in and constitute a part of this specification, illustrate embodiments and features of embodiments of the invention, and together with the written description, serve to explain certain principles of the invention.

Figure 1:
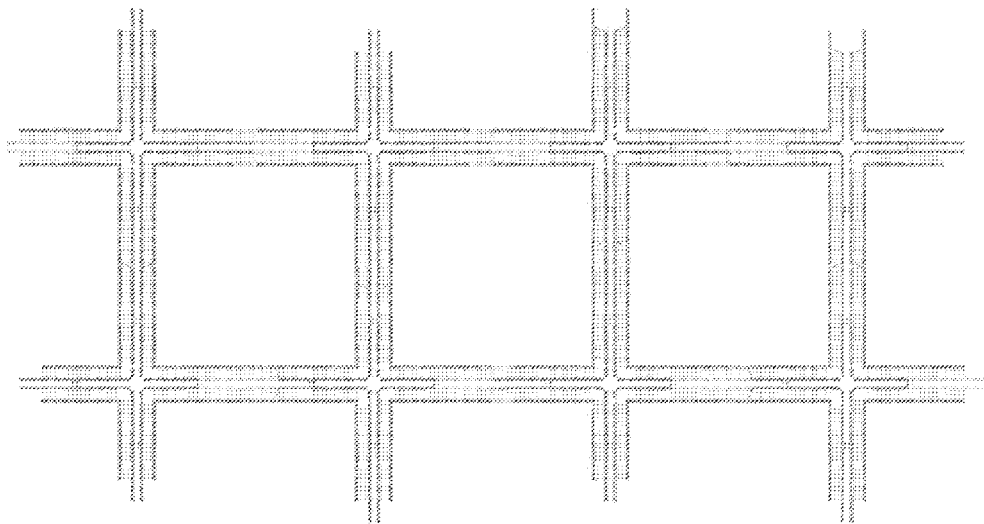
FIG. 1 shows a detailed view of an exemplary DNA nanostructure according to one embodiment of the invention.

Before embodiments of the present invention are described in detail, it is to be understood that the terminology used herein is for the purpose of describing particular embodiments only, and is not intended to be limiting. Further, where a range of values is provided, it is understood that each intervening value, to the tenth of the unit of the lower limit, unless the context clearly dictates otherwise, between the upper and lower limits of that range is also contemplated and disclosed without the need to specifically recite each value individually in this text. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which the term belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the singular forms "a", "an", and "the" include plural referents unless the context clearly dictates otherwise. Thus, for example, reference to "a polymer" includes a plurality of such polymers and reference to "the nanostructure" includes reference to one or more nanostructures and equivalents thereof known to those skilled in the art, and so forth. Furthermore, the use of terms that can be described using equivalent terms include the use of those equivalent terms. Thus, for example, the use of the term "subject" is to be understood to include the terms "patient", "animal", "human", and other terms used in the art to indicate one who is subject to a medical treatment. As another example, the use of the term "neoplastic" is to be understood to include the terms "tumor", "cancer", "aberrant growth", and other terms used in the art to indicate cells that are replicating, proliferating, or remaining alive in an abnormal way. The term "animal" includes humans unless otherwise indicated.

As used herein, a substance bonded, bound, or attached to a nanostructure means at least one atom in the substance associates and/or is constrained with the nanostructure via one chemical bond, multiple chemical bonds, or other types of interactions, including but not limited to polar bonding, covalent bonding, ionic bonding, hydrogen bond, and van der Waals interactions.

The present invention provides nanostructures that can be used, among other things, as physical platforms for delivery of substances to targets. While the invention is described in detail with regard to delivery of biologically active agents (also known in the art as bioactive agents) to target cells, tissues, and organs of subjects, it is to be understood that the nanostructures can be used to deliver any small substance to any target, the only restriction being that the substance to be delivered must be of a sufficiently small size to be capable of binding to the nanostructures of the invention. The substances are thus typically on the order of one micrometer or less in length/diameter. Non-exclusive examples of substances that do not necessarily have biological activity include: metals, metal alloys, and metal containing complexes; minerals and mineral containing complexes; polymeric elastomers; thermosetting resins; natural and synthetic rubbers; and the like.

In general, the nanostructures of the invention can be considered to have two physical and functional portions: 1) a core structure comprised of one or more polymers, which form into core structure subunits, where the core structure or core structure subunit has a three dimensional shape that is engineered by way of deliberate arrangement of the sequence of the monomeric units that make up the polymers; and 2) one or more substances bonded to the core structure. Bonding of the substance(s) to the core structure can be by any suitable means, including, but not necessarily limited to, chemical bonding (e.g., covalent bonding, ionic bonding, hydrogen bonding). The association between the core structure and the substances can be by way of direct bonding of the two to each other or by way of one or more intermediary molecules, such as linker molecules comprising nucleic acids, polypeptides, or carbohydrates.

For example, a DNA nanostructure can be constructed with a biotin and a pair of thrombin aptamers, where the distance between the biotin and the aptamer pair is pre-determined by design. When the concentrations of streptavidin and thrombin are low, the nanostructure displays the streptavidin at the pre-designed site with low occupancy of thrombin in its binding site. When the concentration of thrombin is increased, the chance to find the nanostructure displaying both streptavidin and thrombin on it at the pre-designed sites increases as well.

The core structure can be comprised of any suitable polymer. In exemplary embodiments, it is comprised of nucleic acids, including both single-stranded and double-stranded DNA and RNA. It has been surprisingly found that DNA nanostructures according to the invention are not only stable in vivo, but are also stable enough to deliver a substance of interest (also referred to herein as a "cargo" or "payload") to a target within a living subject in an amount sufficient to treat the subject.

The core structure is designed using computer software and one or more computing devices. Numerous computer programs and software suites are known and used in the art, and the practitioner is free to choose the appropriate programs or suites according to any number of considerations. An exemplary suitable program suite is the inSēquio™ Sequence Design Studio (Parabon NanoLabs, Inc., Reston, Va.). In general, the program or suite of programs must be capable of using known physical and chemical properties of a particular polymer, and specifically the monomeric units making up that polymer within the overall context of the polymer sequence, and determining the types and strengths of interactions between and among the various possible permutations of interacting sequences. By arranging the order of bases within a set of nucleic acid strands, the strands can be "programmed" to assemble into complex designs by way of known complementarity rules. For example, the computer program can design two nucleic acid sequences that provide complementary and non-complementary regions such that a desired shape can be formed.

Although the core structure can comprise a single polymer, it is typically fabricated from multiple polymers, which typically, but not necessarily, form multiple subunits that are ultimately combined to create a final core structure. In an exemplary embodiment of the invention, multiple DNA strands are designed in conjunction with each other such that they interact in a specifically defined way via normal base pairing to form a pre-defined shape, such as a "tile" having fixed junctions. Each of the tile subunits has four possible ends that can serve as binding points for other tiles. Each end has a sequence that is designed to interact (e.g., hybridize) with only one other end of a designated designed tile. If a particular end is destined to be a terminal edge of the nanostructure, the end is designed such that it cannot bind to any end of another tile. In such a way, binding of tiles is completely controlled and the overall structure of the nanostructure can be designed by selection of the various sequences of the DNA strands making up the nanostructure.

Precisely addressable multiple binding effectors or substances allowing for detection of the location of the nanostructures or portions thereof (also referred to herein at times as "substances" or "moieties") can be attached to the nanostructure. Where the moieties act as binding effectors, they can achieve better specificity for their target cells via a multivalent, low affinity approach instead of the usual monovalent, high affinity approach. Nanostructures having such an array of effectors have now been tested and found to accumulate effectively in target cells in vivo and have been found to have biological activity in vitro (see, e.g., FIGS. 4 and 5, discussed in more detail below).

Using a DNA nanostructure as an example representing the full scope of the invention, the DNA core structure is designed to have high stability and high yield at different buffer conditions and ionic strengths, including but not limited to physiological buffer conditions and ionic strength. Also, for in vivo applications, the DNA core structure is typically optimized to be stable over a relatively large temperature range, including but not limited to 4° C. to 50° C., such as, for example, ambient temperature (about 20° C. to about 22° C.) to 37° C. For exemplary embodiments relating to in vitro applications, the core structure can be designed to have high stability over a broader range of temperatures, such as from 4° C. to 80° C. In embodiments relating to medical or diagnostic applications, the nucleic acid sequences of the core structure are specifically assigned to fulfill medical and diagnostic tasks. In the following examples, the core DNA structures have been shown to retain their functionality and activity in vitro and in vivo.

The core structure can be functionalized with different functional groups, including different organic and inorganic molecules, at one or multiple sites, with precisely controlled positions within the polymers making up the core structure. In some cases, however, attempts to functionalize a DNA nanostructure can poorly affect its self-assembly. The functional RGD peptides used for cell targeting in the nanostructure exemplified below have been optimized to be compatible with the assembly of the DNA core structure while ensuring the functionality of the functional group. Each motif or subunit of the core structure is designed to have an identical structure with the other subunits, and DNA sequences at the central part, except the sticky ends. This design ensures all the motifs have identical stability at different buffer conditions and temperatures. The sticky ends are designed with unique sequences that have minimum chance to form undesired base pairings, i.e., non-specific binding with the bases in the nanostructure to ensure the high yield of the nanostructure during self-assembly. Moreover, the two parallel sticky ends on the tip of each arm of the exemplary nanostructure were designed to form 10 base pairs (and longer pairing sticky ends are possible), which provides a strong binding force that helps stabilize the whole construct. The skilled artisan will recognize that the exemplified 10 base pairing scheme is not a limiting feature of the invention, but instead is a bonding length that is generally suitable for stable bonding under physiological conditions.

The GC content for all the sticky ends in a nucleic acid-containing nanostructure is carefully normalized so that the stability of each connection is similar to others and maximized to provide the greatest possible binding strength. This approach ensures that there is no possible weaker connection in the nanostructure that could affect the integrity of the whole construct in different buffer conditions and temperatures.

One or more substances are bound to the core structure. While not so limited, in exemplary embodiments, the substances generally fall into two categories: 1) targeting substances; and 2) bioactive agents. A targeting substance is a substance that has an intrinsic ability to bind to a general class, and more preferably a particular species, of a biological substance, molecule, etc. It thus can be, for example, a ligand for a cell-surface receptor found on a particular type of cell (e.g., neuron, neutrophil, T-cell, muscle cell, tumor cell). Likewise, it could be an antibody that specifically binds to a viral coat protein, an outer membrane protein of Gram negative bacteria, or any other protein expressed on the outer surface of a virus, prokaryote, or eukaryote. In preferred embodiments, the targeting substance specifically binds to a molecule that is present on only one type of cell, such as a particular type of tumor cell.

More specifically, in embodiments, the core structure can be designed and produced with one or more cage-like structures. Bioactive agents can be included and limited in the cage-like structure(s) by the stereo hindrance of the wall of one or more cage-like structures and/or other interactions. The release of the bioactive agents can thus be precisely controlled. For example, the wall of cage-like structure can contain one or more disulfide bonds. A reducing environment, e.g., the cytosol, can induce the breakdown of the disulfide linkage(s), disrupt the wall of the cage-like structure in one or multiple sites, and, therefore, release the bioactive agents from the cage-like structure.

The targeting substance is provided as part of the nanostructure to target the nanostructure to a particular cell, tissue, or organ of interest, such as one involved in a disease or disorder state. In embodiments, the nanostructure comprises two, or more than two, different targeting substances, one that is specific for a certain cell or cell type and another that is specific for a different cell or cell type. For example, the nanostructure can be a generally planar structure having a targeting molecule on one surface (the first surface) that is specific for macrophages, and having a targeting molecule on the other surface (the second surface) that is specific for a Gram negative bacterium. Such a nanostructure can also have a cytotoxic agent on the second surface, which is toxic to Gram negative bacteria. Targeting of the nanostructure to the macrophage assists the nanostructure in localizing to the area of the body in which the Gram negative bacteria has set up an infection, and improves targeting of the Gram negative bacterium for delivery of the cytotoxic agent.

The substance can also be one that allows detection of the nanostructure or a substance that was bound to it during production of the nanostructure. In in vivo settings, detection is typically assayed in terms of the location of the nanostructure or substance within the body of the animal being studied. In in vitro settings, detection can be a simple matter of determining if the nanostructure is bound to the target cell. For example, the substance can be a fluorescent compound, an electron-dense, proton-dense, or other molecule that is preferentially detectable using a scan of wavelengths in the electromagnetic spectrum and/or sonic spectrum, or other methods, where the appropriate scan detects the presence and, preferably for in vivo applications, location of the substance.

The nanostructure of the present invention has wide applicability in the medical treatment field, but also has wide applicability in the clinical diagnostic field as well as in all fields in which detection of a cell surface target substance is desired. That is, because the nanostructures of the present invention can include moieties that are specific for any number of substances, they can be used in detection assays for detection of any number of substances. They thus can be used to detect, in vivo, the size of a tumor by way of specific binding to target tumor cells and production of a detectable signal showing the location of the (bound) nanostructure. Furthermore, because the precise sequence of monomers that make up the polymers that make up the core structure of the nanostructures is known prior to fabrication of the nanostructures, means for detecting the nanostructures, apart from detecting the bound moieties, will be known, and can be used to isolate or detect the nanostructures, when bound to a target substance.

Functionalization of nucleic acid core structures allows for placement of targeting substances, bioactive agents, and the like at predefined sites on the structure. It thus provides for a wide variety of different permutations, which allows for great diversity in design of the nanostructures. For example, three dimensional placement of targeting and bioactive substances can advantageously be used to deliver the bioactive substances to sites of interest in active form. For example, a spherical or tubular nanostructure can be formed in which targeting substances are on the outside of the structure, while the bioactive agent is on the inside, protected from the potentially harsh environment of the body. Delivery of the nanostructure to a target cell, and uptake of the nanostructure into the target cell allows intracellular delivery of the bioactive agent in an intact form. Once inside the cell, the nanostructure can be degraded, for example by exonucleases and endonucleases, thus releasing the bioactive agent within the cell. Those of skill in the art will immediately recognize the advantage of this type of delivery vehicle for delivery of nucleic acids (e.g., siRNA, DNA vaccines, antisense molecules), polypeptides, and even small molecule drugs.

An exemplary embodiment of the invention includes the use of multiple, low affinity targeting molecules on the surface of the nanostructure. The targeting molecules can be all of the same type (e.g., a single antibody) or a mixture of two or more different types of targeting molecules. Preferably, two or more different types of low affinity targeting molecules that are specific for the same target are used. In such a way, very high specificity can be achieved, thus providing a therapeutic treatment with high effectiveness and low side effects. Furthermore, lower toxicity to non-target cells can be achieved.

Of course, multiple different bioactive agents can be bound to the nanostructure surface to provide a high biological response. For example, two bioactive agents that have different modes of actions against a tumor cell can be included in a nanostructure. Complementary cell killing activities can be provided to limit the tumor cell's ability to avoid cell death through development of resistance to the mode of action of one of the agents.

A particular advantage provided by the present invention is use of nanostructures for delivery of pharmaceuticals to target organs, tissues, or cells. The type of pharmaceutical delivered is not particularly limited, although it will be evident that its size must be appropriate for the size of the nanostructures of the invention. As such, the pharmaceutical can be any small molecule drug, a biological (e.g., DNA, RNA, protein), or the like. Non-limiting examples of pharmaceuticals according to the invention include cytotoxic agents, such as chemotherapeutic agents, small interfering RNAs (siRNA), single or double stranded DNA, antibodies, and DNA vaccines. Delivery of siRNA with these nanostructures has been tested and shown to successfully "knock down" bioluminescence in glioma cells engineered with luciferase (U87MG-luc2 cell line).

In a similar manner, the type of targeting molecule is not particularly limited. It thus can be any molecule that provides specific binding to a target of interest, typically a cell of interest. Non-limiting examples of targeting molecules are antibodies, ligands for known cell-surface receptors, hormones, and specific binding partners for non-receptor cell-surface proteins.

In summary, in embodiments the invention provides a nanostructure complex comprising at least one nucleic acid strand, the linear sequences of bases of each being known and artificially and deliberately assigned to cause pre-determined inter- or intra-strand binding to form a pre-determined, finite, two-dimensional or three-dimensional scaffold structure, wherein each strand is of a pre-determined finite length, and wherein each strand may have one or more pre-defined sequences engineered to bond, directly or indirectly by one or more linking substances, possibly affixed to strand terminal modifications, with one or more pre-selected, low-affinity, cell-binding moieties, the collection of which forms a pattern designed to effect highly specific cell binding for targeting the nanostructure complex to designated cell types. In some embodiments, the nanostructure complex includes one or more additional pre-selected substances attached as therapeutic effectors (including, but not limited to siRNA, protein, and small drug molecule), binding effectors (including, but not limited to nucleic acid aptamers, peptides, and organic molecules), immunogenic effectors (including, but not limited to nucleic acids, peptides, and polysaccharides), immunostimulators (including, but not limited to unmethylated DNA CpG motifs, duplex RNA, and lipo-polysaccharides), molecular sensors (including, but not limited to nucleic acid aptamers and antibodies), or bioactive agents (including, but not limited to peptides, nucleic acids, and proteins). The substance(s) can be covalently bonded to the nucleic acid(s). The therapeutic effector includes, but not limited to, siRNA, protein, organic molecule/complex, and inorganic molecule/complex. The binding effector includes, but is not limited to, a nucleic acid aptamer, a protein, a polypeptide, a polysaccharide, a cholesterol, or other organic/inorganic molecules and/or complexes. In embodiments of the nanostructure complex, all of the substances can be the same, all can be different, or some the same and others different. Further, the identity and positioning of the nucleic acid bases, strands, or attachments can be selected to achieve one or more desired physical properties, such as size, conformation, overall charge, charge distribution, hydrophobicity, and hydrophilicity. The pre-defined portion(s) of the nucleic acid(s) can be engineered to control the orientation, conformation, and/or relative positions of the pre-selected substance(s). In some embodiments, the complex has an upper and a lower surface, wherein the complex has at least one pre-selected substance on each of the upper and lower surfaces. In general, the complex has a pre-defined three-dimensional structure having a longest dimension of from 2 nm to 1000 nm.

Yet further, in embodiments the invention provides a method of treating a subject in need thereof, where the method comprises: administering a nanostructure complex of the invention to the subject in an amount sufficient to provide a treatment effect. The treatment effect can be a prophylactic effect or a therapeutic effect. The nanostructure complex can be administered as an immunogen, a vaccine, an immunostimulator, or as a vaccine adjuvant. In embodiments, the method is a method of treating cancer, such as a glioma, breast cancer, prostate cancer, or lung cancer. In some methods of treating, at least one surface of the nanostructure complex is bound by a substance that binds red blood cells and at least one other surface is bound by a substance that binds cancer cells. Alternatively or in addition, the nanostructure complex further can be bound to a cytotoxic agent on one or more of its surfaces. In some embodiments, by virtue of a highly ordered arrangement of immunogenic effectors, the complex promotes a rapid and effective antigen-specific immunogenic response. According to the method of the invention as practiced with nucleic acid complexes, the nanostructure complex comprises nucleic acid strands that are completely complementary with one another, having no unbound nucleotides at either end, which increases the circulation half-life as compared to nanostructures with one or more ends with unbound nucleotides. In exemplary embodiments, the nanostructure complex comprises two or more different substances that are specific for the same target. In some embodiments, the method is practiced using a nanostructure complex that comprises a generally tubular shape defined by an outer surface and an inner surface, wherein the pre-selected substance is bound to the inner surface by disulfide linkages that are reduced upon entry of the nanostructure complex into a cell of the subject.

Yet again, the invention provides a nanostructure comprising: i) a core structure comprising at least two strands of DNA such that each comprising strand has at least one region of at least ten nucleotides which is complementary with at least one other comprising strand (i.e., there are no "isolated" strands that lack complementarity to the core structure), wherein one or more of the DNA strands is functionalized such that the combination of all strands contains at least one binding site for each of at least one targeting molecule and at least one bioactive agent, ii) at least one targeting effector, and iii) at least one bioactive agent; wherein the targeting effector(s) and bioactive agent(s) are bound to the core structure. The targeting molecules can be low affinity binding molecules that are specific for a tumor cell, such as a glioma cell. The nanostructure can have a half life in vivo of at least 2.7 hours.

The invention further provides a method of synthesizing a nanostructure complex having up to 7,000 pre-selected substances bound to the polymer(s). The method comprises reacting amino groups of the polymer(s) of the complex with succinimidyl hemidithiodiglycolyl polyethyleneimine (SHDT-PEI) at an approximate ratio <1:5 in HEPES buffer, pH 8.0, to form a polymer-PEI; covalently bonding the pre-selected substances to the PEI moiety of the polymer-PEI an approximate ratio >5:1 (substance:polymer-PEI); and optionally purifying the complex.

EXAMPLES

The invention will be further explained by the following Examples, which are intended to be purely exemplary of the invention, and should not be considered as limiting the invention in any way.

Example 1

Construction of a Class of "PNL24" DNA Nanostructures

The oligonucleotides (elsewhere abbreviated as oligomers or oligos) for PNL24 complexes were synthesized using conventional phosphoramidite chemistry on controlled-pore glass (CPG) solid support at a synthesis scale of 1 micromole. After synthesis, the raw oligomers were reverse-phase purified and desalted by HPLC. Two functionalized variants of PNL24, described below, were used for in vitro and in vivo testing. PNL24-D is a PNL24 molecule functionalized with fluorescent dyes (D) to enable FRET imaging (FRET imaging usually involves sets of two or more fluorescent dyes or dye and dye quencher sets which enable both localization through determination of the location of the fluorescence signal and enable distance between dyes to be determined, here designed to be used as both a location indicator and as an indicator of structural integrity). PNL24-RD is equivalent to PNL24-D, except it is further functionalized with RGD peptide (R), a known targeting agent for glioma tumor cells. Hereafter, the term "PNL24" is used as shorthand to describe both of these variants without distinction. To produce PNL24-R, an additional amine group was added at the functionalization site of those oligos designated to localize RGD targeting peptide. Conjugation was performed in aqueous buffer (pH 6.0) against excess NHS-ester functionalized moieties. Different conjugation methods and conditions can be used to attach the targeting moieties to the nanostructures. For example, click chemistry between azide and hexynyl has been used to conjugate RGD peptide to Core DNA.

Figure 2:
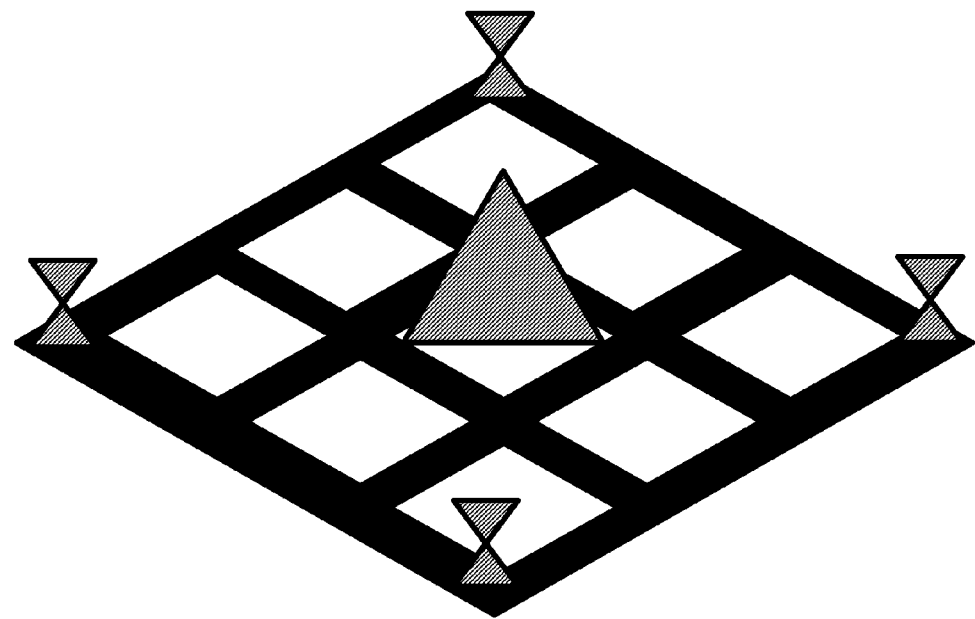
FIG. 2 shows a cartoon rendering of a generally planar DNA nanostructure according to one embodiment of the invention, in which multiple low affinity targeting substances (hourglass-shaped features) are disposed on the planar surface of the core DNA structure along with a single cytotoxic agent (triangular shaped feature).

The structure of PNL24 is illustrated in detail in FIG. 1, and a cartoon form of PNL44 (comprised of two PNL24 molecules joined along one edge) is shown in FIG. 2. Two types of PNL24 compounds (grids) were assembled for in vivo and in vitro studies. The first is referred to as PNL24-R, a DNA grid functionalized with eight RGD peptides as targeting moieties. The sequence of the RGD peptide used in the studies is: GRGDSP (SEQ ID NO:1). The second compound is referred to as PNL24-R-D, a grid with eight RGD peptides and eight Cy™5.5/Cy™7 FRET pairs. Each compound was annealed in a buffer, designed to have the same ionic composition and strength as balanced saline solution, containing: 40 mM Tris, 20 mM Acetic Acid, 1 mM EDTA, 11 mM Magnesium Chloride, and 108 mM Sodium Chloride.

The names and sequences of the DNA oligonucleotides used to produce the PNL24 complexes are as follows (written from 5' to 3'):

CORE:

(SEQ ID NO: 2)
aggcaccatcgtaggttttcgttgcgatcaccaacggagtttttt ctgccgtacaccagtgaagtttttcgatcctagcacctctggagt ttttcttgcc.

CORE-RGD:
(SEQ ID NO: 3)
aggcaccatcgtaggtt(GRGDSP-)
ttcgttgcgatcaccaacggagttttttctgccgtacaccagtgaag
ttttcgatcctagcacctctggagttttttcttgcc.

SHELL1:
(SEQ ID NO: 4)
atgcaacctgcctggcaagactccagaggactactcatccgt.

SHELL2:
(SEQ ID NO: 5)
tccgactgagccctgctaggatcgacttcactggaccgttctaccga.

SHELL3:
(SEQ ID NO: 6)
accggaggcttcctgtacggcagaactccgttggacgaacag.

SHELL4:
(SEQ ID NO: 7)
atagcgcctgatcgcaacgcctacgatggacacgccg.

SHELL1-Cy7:
(SEQ ID NO: 8)
(Cy7-)atgcaacctgcctggcaagactccagaggactactcatccgt.

SHELL2-Cy55:
(SEQ ID NO: 9)
tccgactgagccctgctaggatcgacttcactggaccgttcta
ccga(-Cy55).

SHELL3-Cy55:
(SEQ ID NO: 9)
(Cy55-)accggaggcttcctgtacggcagaactccgttggacgaacag.

SHELL4-Cy7:
(SEQ ID NO: 10)
atagcgcctgatcgcaacgcctacgatggacacgccg(-Cy7).

ARM1:
(SEQ ID NO: 11)
gttatcggcgtgtggttgcataatac.

ARM2:
(SEQ ID NO: 12)
caatcacggatgagtagtgggctcagtcggacattc.

ARM3:
(SEQ ID NO: 13)
cctcgtcggtagaacggtggaagcctccggtcgtgc.

ARM4:
(SEQ ID NO: 14)
ttcaactgttcgtggcgctatattgt.

ARM5:
(SEQ ID NO: 15)
caagccggcgtgtggttgcatacgac.

ARM6:
(SEQ ID NO: 16)
aagtgacggatgagtagtgggctcagtcggatactg.

ARM7:
(SEQ ID NO: 17)
ttgattcggtagaacggtggaagcctccggtttaca.

ARM8:
(SEQ ID NO: 18)
gattgctgttcgtggcgctatgaatg.

ARM9:
(SEQ ID NO: 19)
cgaggcggcgtgtggttgcatgcacg.

ARM10:
(SEQ ID NO: 20)
ttaagacggatgagtagtgggctcagtcggattgta.

ARM11:
(SEQ ID NO: 21)
tcatgtcggtagaacggtggaagcctccggtttgct.

ARM12:
(SEQ ID NO: 22)
tgtagctgttcgtggcgctattacgt.

ARM13:
(SEQ ID NO: 23)
tctgacggcgtgtggttgcattcaac.

ARM14:
(SEQ ID NO: 24)
ctacaacggatgagtagtgggctcagtcggaacgta.

ARM15:
(SEQ ID NO: 25)
gcttgtcggtagaacggtggaagcctccggtgtcgt.

ARM16:
(SEQ ID NO: 26)
taacgctgttcgtggcgctatcattg.

ARM17:
(SEQ ID NO: 27)
catgacggcgtgtggttgcatagcaa.

ARM18:
(SEQ ID NO: 28)
aacgtacggatgagtagtgggctcagtcggactaac.

ARM19:
(SEQ ID NO: 29)
tgctgtcggtagaacggtggaagcctccggttgcag.

ARM20:
(SEQ ID NO: 30)
tcattctgttcgtggcgctattcaat.

ARM21:
(SEQ ID NO: 31)
ctgtgcggcgtgtggttgcattgcac.

ARM22:
(SEQ ID NO: 32)
atgctacggatgagtagtgggctcagtcggaatgac.

ARM23:
(SEQ ID NO: 33)
tcagatcggtagaacggtggaagcctccggtgttga.

ARM24:
(SEQ ID NO: 34)
acgttctgttcgtggcgctatgttag.

ARM25:
(SEQ ID NO: 35)
cagcacggcgtgtggttgcatctgca.

ARM26:
(SEQ ID NO: 36)
ttagaacggatgagtagtgggctcagtcggattagt.

ARM27:
(SEQ ID NO: 37)
aatagtcggtagaacggtggaagcctccggttagat.

ARM28:
(SEQ ID NO: 38)
agtacctgttcgtggcgctattcaca.

ARM29:
(SEQ ID NO: 39)
taactcggcgtgtggttgcattgtat.

-continued

ARM30:
(SEQ ID NO: 40)
gtactacggatgagtagtgggctcagtcggatgtga.

ARM31:
(SEQ ID NO: 41)
cacagtcggtagaacggtggaagcctccggtgtgca.

ARM32:
(SEQ ID NO: 42)
tctagctgttcgtggcgctattagct.

The PNL24 molecules ("grids") are assembled from eight "+" shaped motifs. One motif has one core DNA strand, four shell DNA strands and four arm DNA strands. All experiments are under sterile conditions. Each motif is annealed separately at first. The core strand, shell strands, and arm strands of each motif are mixed stoichiometrically to reach 1 uM concentration in aqueous buffer with 40 mM Tris, 20 mM Acetic Acid, 1 mM EDTA, 11 mM Magnesium Acetate, and 108 mM Sodium Chloride (1×TAE/Mg$^{2+}$ buffer, 108 mM NaCl, pH=8.0). The mixture is then heated to 95° C., then cooled down to 4° C. slowly over 24 hours and kept at 4° C. for 12 hours to stabilize the motif structure. After separately assembling the eight types of motifs, they are mixed in stoichiometric quantities and annealed from 30° C. to 22° C. over 4 hours. Then, the sample is incubated at 4° C. for 12 hours to further stabilize the 2×4 grids. The assembly of PNL24 compounds and other nanostructures in the invention can be achieved in a wide range of different conditions. For example, the pH can typically be between 7 and 10. The Mg$^{2+}$ concentration can be at least between 10 mM and 100 mM. The buffer can use hepes to replace Tris.

Example 2

In Vitro Toxicity Testing

For each in vitro toxicity test, U87MG cells were divided into two groups: a control group and a treated group. Each group had six wells. Each well contained 300 uL medium. After the multi-well plate with medium was incubated in a CO$_2$ incubator at 37° C. in 5% CO$_2$ and 100% humidity for two hours to reach equilibrium with the environment, 5×10$^4$ U87MG cells were seeded in each well and incubated for 24 hours to allow the cells to adhere to the bottom of the wells. Thereafter, the media in the treated group was replaced with a 300 uL mixture of fresh media and PNL24 complex. The media in the control group wells was changed to a 300 uL mixture of fresh media and buffer. After a 24-hour incubation, the media in both groups was changed to a mixture of 250 uL fresh media and 50 uL of CellTiter 96 AQueous One Solution (Promega, Cat. #: G3582) in each well. A no-cell control with 300 uL of the mixture was also added in an empty well. The multiwell plate was further incubated for 4 hours at 37° C. in 5% CO$_2$.

Figure 3:
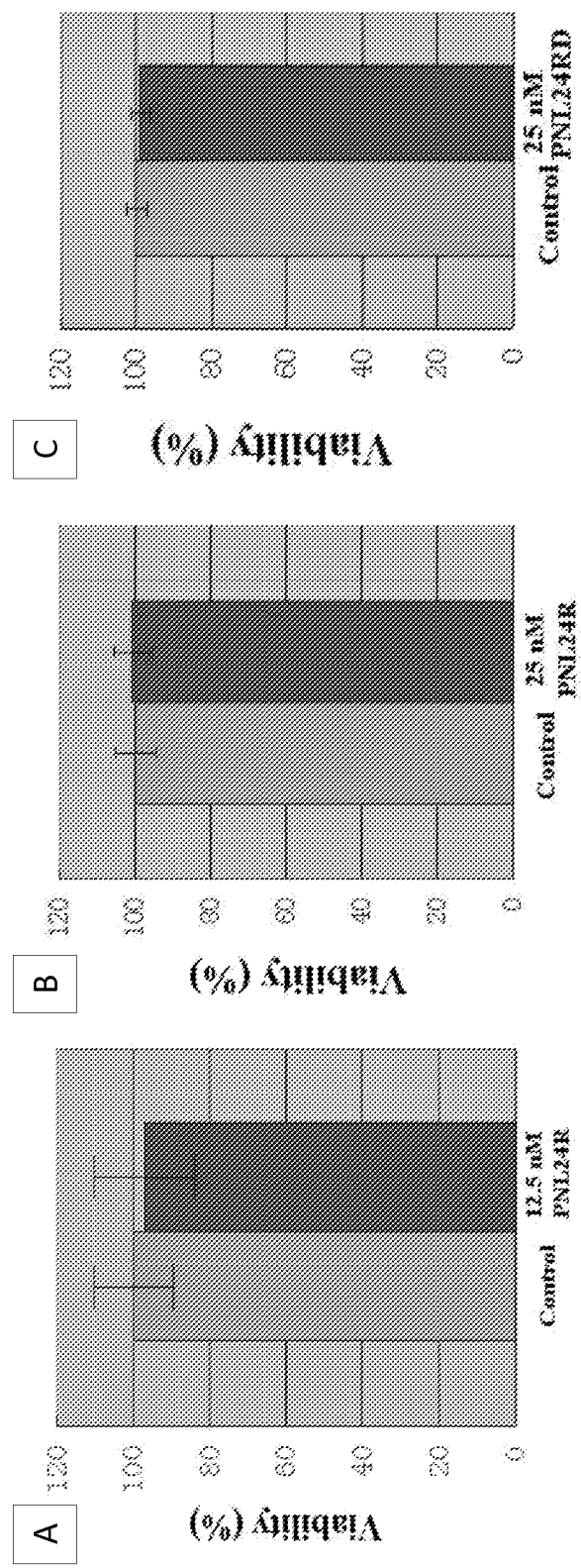
FIG. 3 presents bar graphs showing the results of in vitro toxicity studies using a colorimetric viability assay on U87MG cells. Panel A shows the viability of U87MG cells treated with 12.5 nM PNL24-R (13 mg/kg) vs. untreated control cells. Panel B shows the viability of U87MG cells treated with 25 nM PNL24-R (26 mg/kg) vs. untreated control cells. Panel C shows the viability of U87MG cells treated with 25 nM PNL24-RD (26 mg/kg) vs. untreated control cells.

The absorbance at 490 nm of the samples from each well was measured with a ND-1000 uv-vis spectrometer. The background of the no-cell control solution was blanked out before the measurements. FIG. 3 shows the data of the in vitro toxicity studies with PNL24-R in 12.5 nM and 25 nm as well as PNL24-RD at 25 nM. The data demonstrate that neither PNL24-R nor PNL24-RD is toxic to U87 mg cells.

More specifically, an MTS assay (Promega Cat. #: G3582) was conducted to examine the toxicity of PNL24-R (=PNL24 scaffold+RGD targeting ligand) and PNL24-RD (=PNL24-R+FRET Dyes) against U-87 MG glioma cells. Both compounds were shown to be completely benign. The charts in FIG. 3 show negligible difference in the viability of treated and non-treated U-87 MG cells. The LD50 for PNL24-R is therefore greater than 4× the dosage used to show 20× selective targeting (i.e., contrast) of PNL24-RD to U-87 MG with the in vivo murine model (described below). Accordingly, any (unobserved) intrinsic toxicity of PNL24-R and similar nanostructures is not likely to limit the maximum dosage of compounds created using them.

Example 3

Imaging Studies Demonstrating Accumulation in Tumor

The oligonucleotides for PNL24 were synthesized using conventional phosphoramidite chemistry on controlled-pore glass (CPG) solid support at a synthesis scale of 1 micromole. After synthesis, the raw oligomers were reverse-phase purified and desalted by HPLC. To produce PNL24-D and PNL24-RD an additional primary amine group was added at the functionalization site of those oligos designated to localize either a fluorescent probe or RGD targeting peptide (GRGDSP). Conjugation was performed in aqueous buffer (pH 6.0) against excess NHS-ester functionalized moieties. Two fluorescent probes (donor and acceptor) were used to create FRET pairs (Cy5.5™/Cy7™) at each PNL24 motif intersection and a 6-mer linear RGD peptide was used as a targeting molecule attached to the center of each motif in PNL24-RD.

The names and sequences of the DNA oligonucleotides used to produce PNL24 complexes are the same as the sequences in Example 1.

The target grid molecules are assembled from eight "+" shaped motifs. One motif has one core DNA strand, four shell DNA strands and four arm DNA strands. All experiments are under sterile condition. There are two groups of 2×4 grids. In the first group, RGD peptide is attached to the core DNA strands to produce PNL24-RD grids. The core strand in the second group is only regular DNA to assemble PNL24-D. Each motif is annealed separately at first. The core strand, shell strands, and arm strands of each motif are mixed stoichiometrically to reach 1 uM concentration in aqueous buffer with 40 mM Tris, 20 mM Acetic Acid, 2 mM EDTA and 12.5 mM Magnesium Acetate (1×TAE/Mg$^{2+}$ buffer, pH=8.0). The mixture is then heated to 95° C., then cooled down to 4° C. slowly over 24 hours and kept at 4° C. for 12 hours to stabilize the motif structure. After separately assembling the eight types of motifs they are mixed in stoichiometric quantity and annealed at from 30° C. to 22° C. over 4 hours. Then, the sample is incubated at 4° C. for 12 hours to stabilize the 2×4 grids.

The in vivo study was conducted to assess the tumor targeting capability of PNL24-RD versus a control variant, PNL24-D, which lacks RGD targeting ligands. A group of seven (7) matched nude mice were selected on Day 0 of the study. Six (6) of these mice were injected subcutaneously, in the back, with 5×10$^6$ U87 MG Luc2 cells, which have been modified to produce luciferase for bioluminescence imaging. The mice were divided into four groups. In group 1, a mouse without tumor was dosed with 400 ul PNL24-D (250 nmole/L). In group 2, a mouse bearing tumor was used as a control without any treatment. In group 3, the mice bearing tumor were treated with 400 ul PNL24-RD (250 nmole/L). In group 4, the mice with tumors were treated with 400 ul PNL24-D (250 nmole/L).

Bioluminescent and fluorescent images were acquired in vivo at time points of 1, 3, 7, and 24 hours post injection.

The relative size of the tumor was quantitatively determined from these images based on the proportion of luciferase-bearing cells in the tumor. At 30 hours after injection, the tumors, brains, lungs, livers, hearts, spleens, kidneys, and intestines of the animals were excised into solution and these organs were imaged ex vivo. The tumors were imaged both using bioluminescence and fluorescence so that fluorescence of the tumors could be normalized against the bioluminescence of the tumors.

Figure 4:
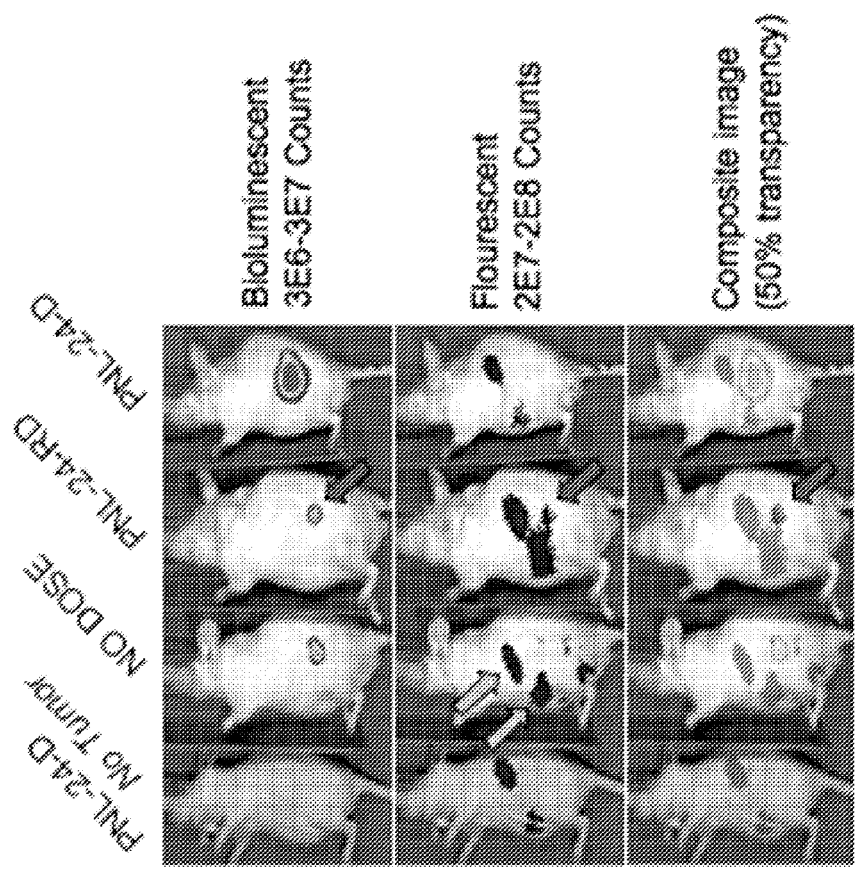
FIG. 4 shows bioluminescence and fluorescence images of mice used as a model system for gliomas and treatment with a DNA nanostructure according to the present invention.
Figure 5:
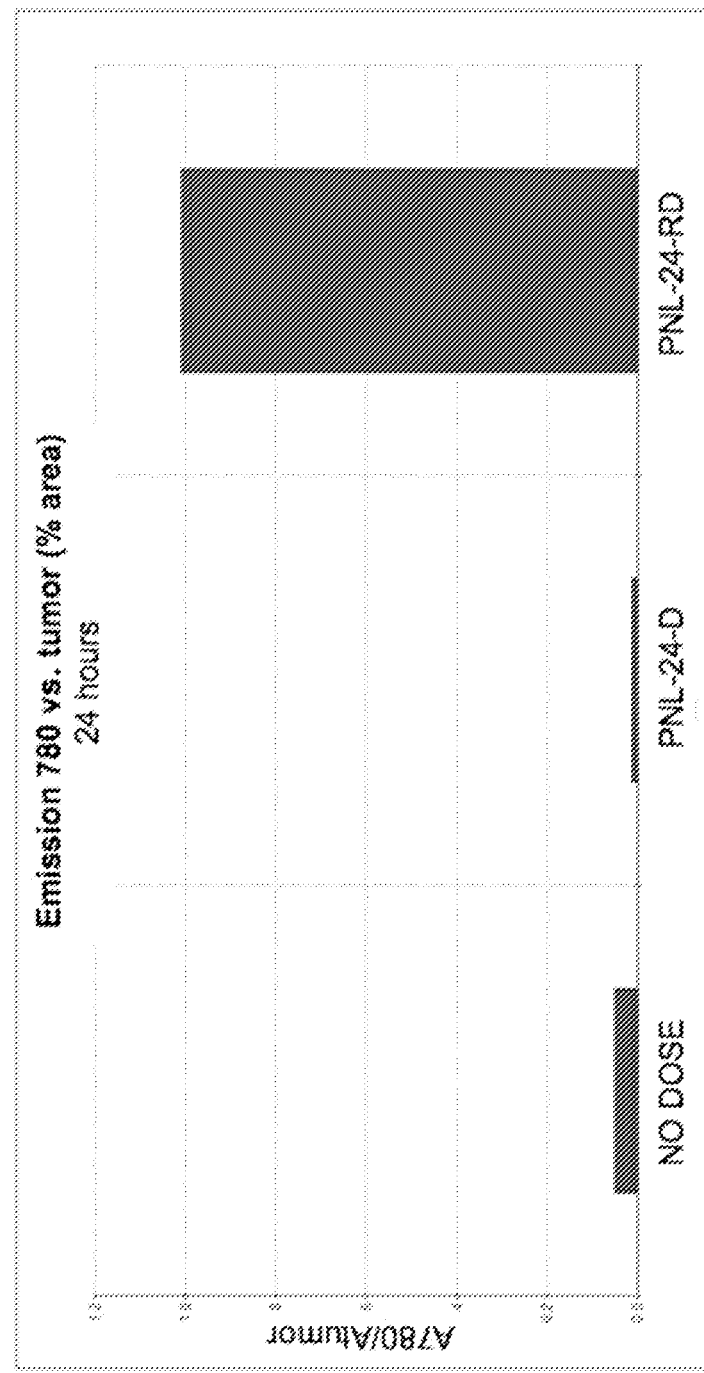
FIG. 5 presents the data from FIG. 4 in a bar graph form.
Figure 5A:
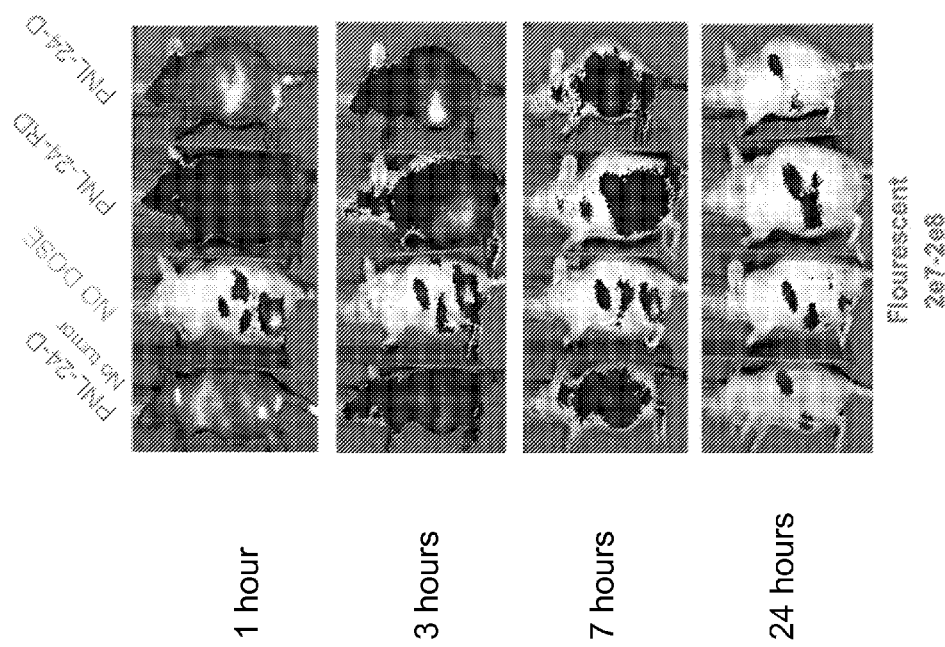

The results are shown in image form in FIG. 4 and in bar graph form in FIG. 5. Specifically, FIG. 4 shows bioluminescent and fluorescent images taken 24 hours after administration of PNL24-D and PNL24-RD. The non-dosed specimen in the fluorescent image shows naturally occurring emissions from the spleen and gut (arrows), which are also apparent in the dosed specimens. Only the specimen treated with PNL24-RD (arrow), which contains the RGD peptide targeting moiety, shows accumulation at the tumor site, as can be seen in the composite overlay image. Fluorescent images taken at 1, 3, 7, and 24 hours clearly indicated pervasive circulation and distribution of the compound as shown in FIG. 5a. Active (FRET producing) constructs were observed at 7 and even 24 hours post injection. The first order decay curve fit to this data indicates a tissue half-life for the FRET emitting component of 2.7 hours. This was an important finding because, before this study, it was not known how rapidly these nanostructures would be removed from circulation. It is possible that longer tissue and circulation half-life can be achieved with PEGylation and other straightforward modifications. By 24 hours, only limited background fluorescence remained, and the labeling of the tumor by the experimental compound can be readily recognized (FIG. 4). These data suggest that a dosing level of ½₀th of what was used could achieve optimal contrast after about 1 hour and be cleared in about 8 hours.

The results obtained in this study are consistent with (a) targeting of the constructs to the site of the tumor, (b) maintenance of intact FRET capability, and (c) stabilization of the relative locations of grid components at the tumor site, for at least 24 hours. This long term structure stability, in a biologically relevant environment, suggests a mechanism of application for these structures that is unique in that programmable structures can be activated after the majority of them have been cleared from sensitive tissues. This is not a property of small drugs or most drug carriers.

As described above, the tumors and major organs were excised into solution and imaged. The tumor was imaged using bioluminescence and fluorescence (Table 1). Because the tumor sizes were not equal in all animals, fluorescence of the tumors was normalized against the tumor's bioluminescence. The tumor receiving PNL24-RD was the only tumor to display a fluorescent signal above background. For comparison purposes, the uncorrected fluorescence signal was used in generating the final fluorescence signal normalized to the tumor bioluminescence. The targeted compound displayed 20× the normalized fluorescent signal.

TABLE 1

Fluorescent and Bioluminescent Levels of Tumors at 30 Hours

| | No Treatment (background) | PNL24-D (no tumor) | PNL24-RD (tumor) | PNL24-D (tumor) |
|---|---|---|---|---|
| Fluorescence | 1.2E+07 | 9.5E+06 | 2.0E+07 | 1.1E+07 |
| Fluorescence w/o background | 0 | below background | 8.3E+06 | below background |
| Bioluminescence | 7.1E+07 | N/A | 5.1E+07 | 6.7E+08 |
| Bioluminescence/ Fluorescence | 0.17 | N/A | 0.4 | 0.02 |

Together, these data provide the first evidence that DNA nanostructures can serve as the basis for creating multifunctional nano-pharmaceuticals.

Example 4

A Nanostructure Delivery Vehicle for Diphtheria Toxin

Diphtheria toxin (DT) is an exotoxin of diphtheria, an acute infectious disease caused by the bacteria *Corynebacterium diphtheriae*. When fused with interleukin-2 protein, DT subcomponents have been approved by the FDA as an antineoplastic agent for the treatment of cutaneous T-cell lymphoma under the name denileukin diftitox (Ontak®). DT is a protein with 535 amino acid residues consisting of two subunits, A and B, that are bound covalently with a disulfide bond. The A subunit, DTA, is highly cytotoxic intracellularly—a single DTA molecule is often sufficient to effect mammalian cell death—however, it is non-endocytotic and harmless extracellularly. The B subunit, DTB, is responsible for effecting cell entry in naturally occurring DT.

DTB has two major domains: 1) receptor binding domain and 2) transmembrane domain. The receptor domain recognizes and binds to heparin-binding epidermal growth factor on the surface of DT-sensitive cells, which in turn leads to the endocytosis of the DT complex. Translocation of DTA into the cytosol is effected by low-pH-triggered insertion of the transmembrane domain into the endosomal membrane. After release, DTA halts the RNA translation step of cellular protein synthesis by catalytically removing the ADP-ribose unit from eukaryotic elongation factor-2 (eEF2) protein via NAD+-diphthamide ADP-ribosyltransferase activity and thereby destroys the cell. In summary, DTA is non-endocytotic, harmless until cell entry and potent thereafter. Moreover, it is highly stable, remaining intact at 100° C. or in a solution with a pH range from 2-12. Importantly, in an alternative formulation, it has been approved by the FDA as a cancer treatment. Accordingly, by attaching DTA to a tumor selective nano-carrier that can effect endocytosis (replacing the role of DTB in natural DT function), DTA can potentially be used as a safe yet highly effective anti-cancer cytotoxic payload.

DTA is attached to a P25 theranostic molecule, a PNL24 variant designed to target glioma cells with high specificity, deliver a cytotoxic payload and carry a contrast-enhancing tracer to facilitate MRI tracking of tumor extent and treatment response. DTA is attached to the PNL24 scaffold via a disulfide bond (—S—S—), a covalent conjugation of two sulfhydryl groups (—SH) via oxidation. 5' aminated SHELL4 DNA can first react with the NHS ester on sulfo-LC-SPDP and then react with the sulhydryl group of cysteine to form disulfide bond. The conjugate is purified with gel electrophoresis. The disulfide bond can be broken into two sulfhydryl groups reversibly when a reductive agent is available. Because the human bloodstream is oxidative and most human intracellular environments are reducing, a disulfide bond can serve as a convenient linker for a drug delivery system that is able to release a therapeutic payload after cell entry. In fact, several natural toxins (e.g., DT and ricin toxin) and FDA approved drugs (e.g., Ontak® and Myobloc®) take advantage of the disulfide linkage for such purpose. Intracellular breakdown of disulfide bonds can occur on the cell surface, in the early endosome, in the cytosol, and in the late endosome or lysosome hybrid. Although the endocytic mechanism of P25 molecules is not yet deeply studied, previous in vivo and ex vivo studies have shown that P25 molecules bearing no targeting RGD peptide had little accumulation in tumors while P25+RGD had significant accumulation in tumors. Based on these experimental results, the binding and internalization of P25 to tumor cells can be highly regulated based on the targeting moieties used, e.g., RGD peptides. Because targeting moieties can also control the endocytic pathway, it is reasonable to believe that the endocytosis of P25DTA into tumor cells can also be controlled by the RGD peptides via cell-adhesion-molecule-mediated pathways.

There is further evidence that linear RGD peptides enter tumor cells and accumulate in the lysosome of tumor cells. This evidence suggests that P25, targeted by linear RGD peptides, can also transfer to the lysosome to deliver disulfide linked DTA. The acidic conditions maintained in the late endosomal compartment ensure that the DTA will be cleaved from P25 and delivered as a native toxin, once the lysosome disassembly process is complete, inducing apoptosis.

The names and sequences of the DNA oligonucleotides used to produce P25DTA complex are listed as following (written from 5' to 3'):

CORE-RGD:
(SEQ ID NO: 43)
aggcaccatcgtaggtt(GRGDSP-)
tcgttgcgatcaccaacggagtttttctgccgtacaccagtgaagtttt
tcgatcctagcacctctggagtttttcttgcc.

SHELL1:
(SEQ ID NO: 44)
atgcaacctgcctggcaagactccagaggactactcatccgt.

SHELL2:
(SEQ ID NO: 45)
tccgactgagccctgctaggatcgacttcactggaccgttctaccga.

SHELL3:
(SEQ ID NO: 46)
accggaggcttcctgtacggcagaactccgttggacgaacag.

SHELL4:
(SEQ ID NO: 47)
atagcgcctgatcgcaacgcctacgatggacacgccg.

SHELL4DTA:
(SEQ ID NO: 48)
(DTA-)atagcgcctgatcgcaacgcctacgatggacacgccg.

ARM1:
(SEQ ID NO: 49)
gttatcggcgtgtggttgcataatac.

ARM2:
(SEQ ID NO: 50)
caatcacggatgagtagtgggctcagtcggacattc.

-continued

ARM3:
(SEQ ID NO: 51)
cctcgtcggtagaacggtggaagcctccggtcgtgc.

ARM4:
(SEQ ID NO: 52)
ttcaactgttcgtggcgctatattgt.

ARM5:
(SEQ ID NO: 53)
caagccggcgtgtggttgcatacgac.

ARM6:
(SEQ ID NO: 54)
aagtgacggatgagtagtgggctcagtcggatactg.

ARM7:
(SEQ ID NO: 55)
ttgattcggtagaacggtggaagcctccggtttaca.

ARM8:
(SEQ ID NO: 56)
gattgctgttcgtggcgctatgaatg.

ARM9:
(SEQ ID NO: 57)
cgaggcggcgtgtggttgcatgcacg.

ARM10:
(SEQ ID NO: 58)
ttaagacggatgagtagtgggctcagtcggattgta.

ARM11:
(SEQ ID NO: 59)
tcatgtcggtagaacggtggaagcctccggtttgct.

ARM12:
(SEQ ID NO: 60)
tgtagctgttcgtggcgctattacgt.

ARM13:
(SEQ ID NO: 61)
tctgacggcgtgtggttgcattcaac.

ARM14:
(SEQ ID NO: 61)
ctacaacggatgagtagtgggctcagtcggaacgta.

ARM15:
(SEQ ID NO: 62)
gcttgtcggtagaacggtggaagcctccggtgtcgt.

ARM16:
(SEQ ID NO: 63)
taacgctgttcgtggcgctatcattg.

ARM17:
(SEQ ID NO: 64)
catgacggcgtgtggttgcatagcaa.

ARM18:
(SEQ ID NO: 65)
aacgtacggatgagtagtgggctcagtcggactaac.

ARM19:
(SEQ ID NO: 66)
tgctgtcggtagaacggtggaagcctccggttgcag.

ARM20:
(SEQ ID NO: 67)
tcattctgttcgtggcgctattcaat.

ARM21:
(SEQ ID NO: 68)
ctgtgcggcgtgtggttgcattgcac.

ARM22:
(SEQ ID NO: 69)
atgctacggatgagtagtgggctcagtcggaatgac.

ARM23:
(SEQ ID NO: 70)
tcagatcggtagaacggtggaagcctccggtgttga.

ARM24:
(SEQ ID NO: 71)
acgttctgttcgtggcgctatgttag.

ARM25:
(SEQ ID NO: 72)
cagcacggcgtgtggttgcatctgca.

ARM26:
(SEQ ID NO: 73)
ttagaacggatgagtagtgggctcagtcggattagt.

ARM27:
(SEQ ID NO: 74)
aatagtcggtagaacggtggaagcctccggttagat.

ARM28:
(SEQ ID NO: 75)
agtacctgttcgtggcgctattcaca.

ARM29:
(SEQ ID NO: 76)
taactcggcgtgtggttgcattgtat.

ARM30:
(SEQ ID NO: 77)
gtactacggatgagtagtgggctcagtcggatgtga.

ARM31:
(SEQ ID NO: 78)
cacagtcggtagaacggtggaagcctccggtgtgca.

ARM32:
(SEQ ID NO: 79)
tctagctgttcgtggcgctattagct.

The oligonucleotides for the P25DTA complex are synthesized using conventional phosphoramidite chemistry as described above. The P25DTA molecules are assembled as described above.

Example 5

A Nanostructure as an MRI Contrast Agent

Nuclear magnetic resonance imaging or magnetic resonance imaging (MRI) is one of the most effective medical technologies for tumor imaging, including brain tumor imaging. The lack of radiation burden strongly recommends MRI as a radiological technique. The resolving power of MRI in some systems can be about 100 microns, roughly the length of a single GBM cell. In different tissues and circumstances, several differences among protons can be detected using an MRI instrument. For example, the spin density, T1 and T2 relaxation times and flow and spectral shifts of protons in different tissues can be used to construct images in different tissues. However, in many cases, the differences are too small to provide useful information. In these cases, contrast agents are used to improve differentiation within MRI image. Based on the mechanism of function, MRI contrast agents can be generally categorized into two broad types: 1) contrast agents with the ability to shorten the T1 relaxation time of surrounding protons; and 2) contrast agents with the ability to shorten the T2 relaxation time of nearby protons. T1 is the spin-lattice relaxation time of the flipped nuclei, while T2 is the spin-spin relaxation time. They are important time constants in MRI. Gadolinium based paramagnetic MRI contrast agents, such as Gd-DTPA, belong to type 1. Gadolinium(III) has seven unpaired electrons, which facilitates the rapid longitudinal relaxation of surrounding excited protons. The rapid relaxation results in a T1 hypersignal. Tissue accumulation of Gadolinium(III) leads to brighter images in T1 weighted MRI.

Gadolinium based MRI contrast agents are the most widely used MRI contrast agents. In fact, Gd-DTPA is FDA approved as an MRI contrast agent and marketed with brand name Magnevist®. Gd-DTPA has also been conjugated with other molecules as a tracer for MRI. Seeing that Gadolinium (III) enhances the contrast of MRI by accelerating longitudinal 1H relaxation, mostly in the nuclei of nearby water, there are generally two approaches to improving contrast: 1) increase the number of exchangeable water molecules in the inner-coordination sphere; and 2) increase the local concentration of Gd(III). Approach 1) generally results in decreasing the stability of the chelated Gd(III) complex. One Gd(III) can bind up to nine ligands. In the contrast agent GD-DTPA, eight ligands are from the chelating compound (DTPA). Only one position is available for the binding of a water molecule. Increasing the number of water ligands would reduce the number of ligands from the chelating molecule binding with the Gd(III), lowering the binding of the chelating agent, and potentially freeing the Gd(III) from the complex. Free Gd(III) ion is a heavy metal ion that is toxic. Therefore, for safety reasons and in order to maximize contrast through maintaining complex integrity, it is difficult to identify a Gd-based contrast agent superior to Gd-DTPA using the first approach.

The nano-theranostic P25 nanostructure complex can enhance contrast of MRI tumor images via the increase of local Gd(III) concentration. Each P25 complex can carry 30 Gd-DTPA molecules. More importantly, the PNL24 platform bearing targeting moieties has been able to reach a 20:1 accumulation on in vivo tumors versus the complex without a targeting system (see above) and this specificity increases the contrast of tumor cells dramatically. Not only can P25 trace primary tumors, but also metastases. Incorporation of DTPA into the design will enable Gadolinium to be replaced by alternative metals, for example europium (Eu), in the cases where Gd toxicity is an issue.

The names and sequences of the DNA oligonucleotides used to produce P25DTPA complexes are the same as the sequences in Example 1, with the following exceptions:

SHELL1Gd:
(SEQ ID NO: 80)
(Gd-DTPA-)atgcaacctgcctggcaagactccagaggactac tcatccgt.

SHELL2Gd:
(SEQ ID NO: 81)
(Gd-DTPA-)tccgactgagccctgctaggatcgacttcactgg accgttctaccga.

SHELL3Gd:
(SEQ ID NO: 82)
(Gd-DTPA-)accggaggcttcctgtacggcagaactccgttgg acgaacag.

SHELL4Gd:
(SEQ ID NO: 83)
(Gd-DTPA-)atagcgcctgatcgcaacgcctacgatggacacgccg.

The oligonucleotides for P25DTPA complex are synthesized as described above. Aminated shell DNA strands can react with extra DTPA in the present of EDC. The DNA-DTPA conjugates can be purified with gel electrophoresis. The DNA-DTPA can form stable complex with Gd(III) at 1:1 ratio. The P25Gd molecules are assembled in accordance with the description above. One motif has one core DNA strand, four shell DNA strands with Gd-DTPA and four arm DNA strands.

Example 6

A Nanostructure for RNA Interference In Vitro and In Vivo

The PNL24-R grid complexes used in the Examples disclosed in this document were designed using the inSēquio™ CAD software from Parabon Nanolabs (Reston, Va.). The complex for this Example contains four shell DNA strands, four arm DNA strands, and a core DNA strand in each "+" motif (see, for example, FIGS. 1 and 2). The SHELL4 DNA strand was selected for siRNA attachment. Multiple linear RGD peptides are attached to the PNL24 scaffold to target α5β1 integrins, which are overexpressed in GBM cells. The effectiveness of this GBM targeting system, which differs from most drug targeting systems because it employs multiple, low-affinity targeting moieties instead of fewer high-affinity moieties, has been demonstrated in Phase I clinical trials.

For this Example, control grids were created (PNL24) without RGD targeting. When siRNA is attached, these controls are referred to as PNL24-siRNA whereas the experimental compound is called PNL24-R-siRNA. The present Example shows that nucleic acid nanostructures of the present invention, which contain siRNA molecules, can be used to specifically reduce expression of a luciferase gene within a cell.

The sequence of the pGL4 vector used to establish the U87 mg Luc2 cell line is from Caliper Life Sciences. The sequences of anti-Luc siRNA strands used in the in vitro experiments are:

```
sense:
                                        (SEQ ID NO: 84)
5'-rGrGrA rCrGrA rGrGrA rCrGrA rGrCrA rCrUrU rCrUrU-3'.

anti-sense:
                                        (SEQ ID NO: 85)
5'-rArArG rArArG rUrGrC rUrCrG rUrCrC rUrCrG rUrCrC-3'.
```

In the PNL24-R-siRNA design, anti-luc siRNA is connect to the PNL24-R grid via a disulfide bond, which is reduced by reduction agents in the cell to effect intracellular release of the siRNA.

The names and sequences of the DNA oligonucleotides used to produce PNL24 complexes are the same as the sequences in Example 1 with the following exception:

```
SHELL4siRNA:
                                        (SEQ ID NO: 86)
atagcgcctgatcgcaacgcctacgatggacacgccg (-anti-luc siRNA).
```

The oligonucleotides for the PNL24-R-siRNA complex are synthesized using conventional phosphoramidite chemistry on controlled-pore glass (CPG) solid support at a synthesis scale of 10 micromole. After synthesis, the raw oligomers are reverse-phase purified and desalted by HPLC into conjugation or hybridization buffer. To produce the Core-RGD DNA strand, an additional amine group is added at the functionalization site of those oligonucleotides designated to localize RGD targeting peptide. Conjugation is performed in aqueous buffer (pH 6.0) against excess NHS-ester functionalized moieties.

5' aminated RNA was mixed with Sulfo-LC-SPDP crosslinker at a molar ratio of 1:100 in PBS buffer at pH 7.4 for 12 hours. The primary amine group on the 5' aminated RNA reacted with the Sulfo-NHS ester to get the amide. The RNA was purified with a Dextran Desalting Column to remove unreacted small molecules.

3' thiolated DNA was first treated with TCEP-HCl at a molar ratio of 1:100 for 12 hours to cleave the disulfide bonds. The DNA was purified with a Dextran Desalting Column to remove unreacted TCEP.

The purified DNA and RNA products were mixed 1:3.44 at 75° C. for 1 hour and 4° C. for 12 hours to allow the pyridinyldisulfide on the 3' end of the DNA to react with the sulhydryls on the 5' end of the RNA to form the DNA-RNA conjugate linked with disulfide bond. The DNA-RNA conjugate was purified with a Dextran Desalting Column. The yield of RNA attachment is tested with Quant-i™ RNA Assay Kit (Invitrogen Cat. #: Q10213).

The eight "+" shaped motifs are assembled first. One motif has one core DNA strand, four shell DNA strands and four arm DNA strands. All experiments are under sterile conditions. For all "+" shape motifs, the shell 4-siRNA conjugate replaces the shell-4 DNA. The complementary RNA is also added in stoichiometrically. The core strand, shell strands and arm strands of each motif are mixed stoichiometrically to reach 1 uM concentration in aqueous buffer with 40 mM Tris, 20 mM Acetic Acid, 2 mM EDTA, 12.5 mM Magnesium Acetate, and 105 mM Sodium Chloride (1×TAE/Mg$^{2+}$ buffer, pH=8.0). The mixture is heated to 95° C., then cooled down to 4° C. slowly over 24 hours and kept at 4° C. for 12 hours to stabilize the motif structure.

After separately assembling the eight types of motifs they are mixed in stoichiometric quantity and annealed at from 30° C. to 22° C. over 4 hours. Then, the sample is incubated at 4° C. for 12 hours to stabilize the 2×4 grids. In this case, one single-stranded siRNA payload is covalently attached to the nanostructure. The complementary RNA is carried on the nanostructure by forming non-covalent base pairs with its complement covalently attached to the nanostructure.

About 2×10$^4$ U87MG Luc2 cells per well were seeded onto a 24-well plate. The cells were incubated for 48 hours at 37° C. with 5% CO$_2$ in 300 uL culture media to allow the cells to attach to the wall of the wells. U87MG Luc2 cells were treated with a mixture of 250 uL PNL24-R-siRNA at 125 nM and 250 uL culture medium at 37° C. with 5% CO$_2$ for 72 hours so that the siRNA could be taken up by the cells. Because the yield of DNA-RNA conjugation was not 100%, the siRNA was 6.5 mg/kg for PNL24-R-siRNA and PNL24-siRNA. The control cells were mixed with: a) 250 uL buffer, 250 uL siRNA (1 uM siRNA concentration=6.9 mg/kg), 250 uL PNL24-R (125 nM), or 250 uL PNL24-siRNA (125 nM); and b) 250 uL culture medium. All the samples were in triplicate. Thereafter, U87MG Luc2 cells are lysed with mammalian cell lysis buffer. The cell lysate is recovered for a luciferase activity assay. Light emission by luciferase molecules is measured by a luminometer. The total protein concentration in the cell lysate is determined using the BCA assay. Luciferase activity in each sample is normalized to relative light units (RLU) per mg of cell lysate proteins.

Figure 6:
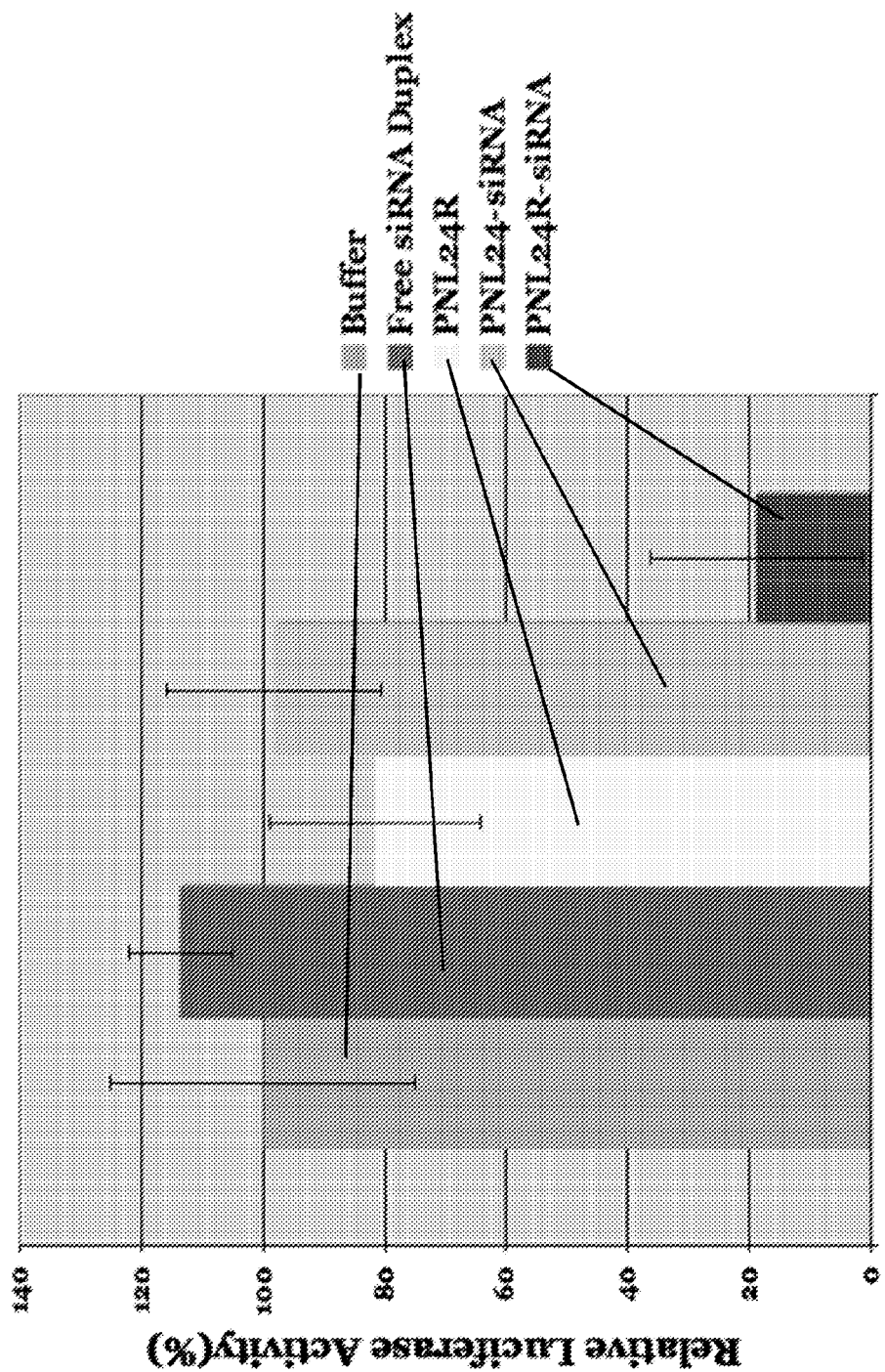
FIG. 6 is a bar graph showing the effectiveness of an siRNA-containing nanostructure according to one embodiment of the invention, which is capable of specifically reducing expression of a target luciferase gene in vitro via transfection of an anti-Luciferase siRNA payload.

FIG. 6 shows that the luciferase activity of PNL24-R control samples is much higher than the normalized luminescence of PNL24-R-siRNA samples (100:23).

The relative luciferase activity of all control groups was significantly higher than the normalized luminescence of PNL24-R-siRNA-treated group. The results demonstrate that PNL24-R-siRNA can effectively knockdown the expression of luciferase in U87 mg Luc2 cells in vitro. As a proof of principal, these results are highly significant. Even though the detailed mechanism of payload internalization is not yet clear, the results indicate an active siRNA payload can overcome all the barriers and be delivered intracellularly.

The PNL24-R-siRNA compound was used to knock down the expression of luciferase in vivo in U87MG-Luc2 xenograft murine model. The mock compound (i.e., PNL24-R) and free anti-Luc siRNA were used as controls.

Eleven (11) male nu/nu mice were implanted with intracranial xenograft tumors, specifically, $1 \times 10^6$ U87MG-Luc2 cells were implanted by stereotaxic injection directly into the caudate/putamen. Mice were anesthetized by intraperitoneal injection of 3 ml/kg of a solution containing 25 mg/ml ketamine HCl, 2.5 mg/ml xylazine, and 14% ethanol in 0.85% NaCl. Surgical sites were prepared with alcohol and betadine. Animals were positioned using a stereotaxic frame with small animal adaptor, the calvarium was exposed and a 1.5 mm burr hole drilled 2 mm lateral and 1 mm anterior to the bregma. Surgery was performed with sterile tools on a sterile surface. Before the treatment phase of the experiment, the mice were housed for seven days to allow the tumors to be established.

For conviction-enhanced delivery (CED) of PNL24-R-siRNA, free siRNA control and PNL24R control, a dosage was infused intracranially with CED one week after the tumor implantation. During the CED process, animals were given 2 ml of warm normal saline i/p and kept on a warming pad prepared immediately after anesthesia induction. CED was performed using 10 µl total perfusate volume for each sample. The CED speed was 300 nl/min. The 33 G needle was initially inserted at −2 mm mark and 1 µl was infused, then needle tip was advanced to −2.5, −3, −3.5, and −4 mm points and 2 ul solution was infused at each site. A "hemostatic pause" of 2-3 minutes was taken after each needle advancement.

The mice were randomly distributed into three groups with four mice/group for the PNL24-R-siRNA treatment group and PNL24-R control group. Three mice were in the siRNA control group. Mice in the three treatment and control groups were dosed intracranially with 10 µl PNL24R-siRNA (2.5 µM), PNL24R control (2.5 µM), and free siRNA control (20 µM), respectively via CED.

Each mouse was imaged with a IVIS 100 System (Xenogen Corporation) to record bioluminescent signal on day 6 after the administration of PNL24-R-siRNA, free siRNA control, or PNL24R control. Imaging followed intraperitoneal injection with D-luciferin (Xenogen Corp.) at a dose of 330 mg/g body weight, along with anesthesia with xylazine/ketamine. Emitted light from the tumor was acquired with the IVIS 100 cooled CCD camera systems. Following observation of sufficient depth of anesthesia, bioluminescent signals were collected for 5-25 minutes after substrate injection.

In this example, all the mice intracranially administered with PNL24 compounds survived for 6 days (until sacrificed) with no observable abnormalities. This observation supports the safety of PNL24 compounds.

Figure 7:
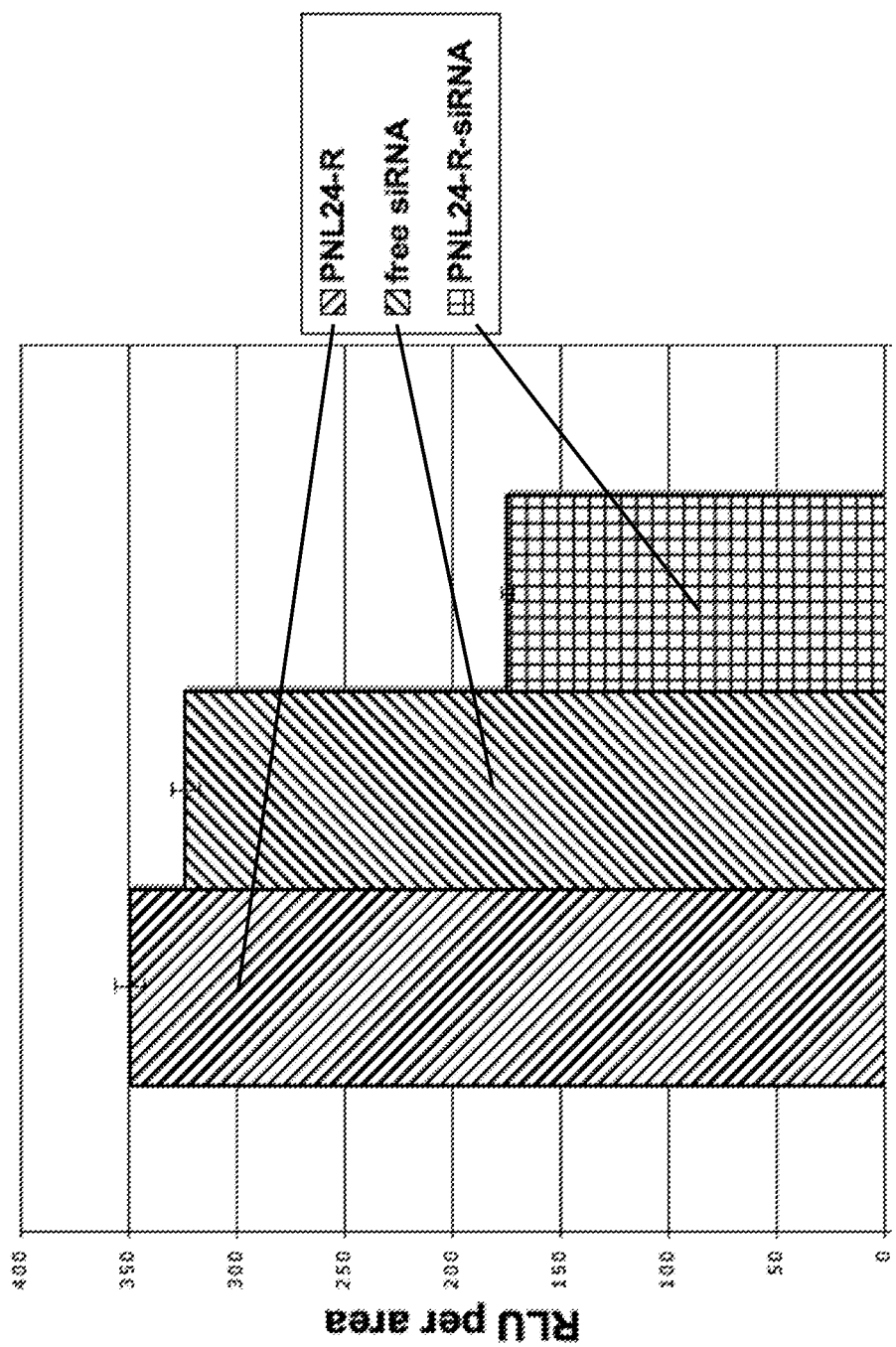
FIG. 7 is a bar graph showing the effectiveness of an siRNA-containing nanostructure according to one embodiment of the invention, which is capable of specifically reducing expression of a target luciferase gene in vivo.

The data in FIG. 7 represent the average bioluminescent intensity per area in each test group±standard deviation. Analyzed with non-paired student t test, the mean luminescent intensity per area in the treatment group is significantly lower than the mean luminescent intensity per area in both control groups (P<0.001). Based on this calculation, the relative knockdown of luciferase with PNL24R-siRNA vs. control was 50%. Because the molecular weight of the siRNA duplex is about 14 kilodaltons, it is possible to deliver other macromolecules with more than 10 kilodalton molecular weight with a similar approach. Coupled with previous results showing that PNL24-R can effectively target GBM tumors in vivo, these results suggest the nanostructures can serve as targeted nanocarriers for a wide variety of siRNA and other payloads useful in a broad range of indications.

Example 7

Nanostructures with Anti-GBM Efficacy In Vivo

Two types of anti-GBM siRNAs were carried by PNL24 DNA nanostructures to construct four different types of PNL24 compounds. One siRNA is Notch-1 siRNA. The other siRNA is DGKa siRNA. The sequences of the anti-GBM siRNA strands are listed in Table 2.

TABLE 2

The sequences of the anti-glioma siRNA strands used in the *in vivo* efficacy studies

| Strand Name | Sequence (from 5' to 3') |
|---|---|
| Notch-1 siRNA sense | rUrGrCrCrGrGrGrArArGrUrGrUr GrArArGrCrGdTdT (SEQ ID NO: 86) |
| Notch-1 siRNA anti-sense | rCrGrCrUrUrCrArCrArCrUrUrCr CrCrGrCrCrAdTdT (SEQ ID NO: 87) |
| DGKA siRNA sense | rGrGrArUrUrGrArCrCrCrUrGrUr UrCrCrUrArAdTdT (SEQ ID NO: 88) |
| DGKA siRNA anti-sense | rUrUrArGrGrArArCrArGrGrGrUr CrArArUrCrCdTdT (SEQ ID NO: 89) |

In this study, a PNL24 nanostructure carrying control RNA strands was constructed as a control. The sequences of the control RNA strands are listed in Table 3.

TABLE 3

The sequences of the control RNA strands used in the *in vivo* efficacy studies

| Strand Name | Sequence (from 5' to 3') |
|---|---|
| Control RNA-1 | rUrUrCrUrCrCrGrArArCrGrUrGrUr CrArCrGrUdTdT (SEQ ID NO: 90) |
| Control RNA-1 complement | rArCrGrUrGrArCrArCrGrUrUrCrGr GrArGrAAdTdT (SEQ ID NO: 91) |

The names and sequences of the DNA oligonucleotides used to produce PNL24 compounds and control are the same as the sequences in Example 1 with the following exception:

CORE-RGD:
(SEQ ID NO: 92)
(GRGDSP)aggcaccatcgtaggttttcgttgcgatcaccaacggagt tttttctgccgtacaccagtgaagttttcgatcctagcacctctgga gtttttcttgcc.

SHELL1-Notch-1 siRNA:
((SEQ ID NO: 92))
atgcaacctgcctggcaagactccagaggactactcatccgt (-Notch-1 siRNA).

SHELL4-DGKa siRNA:
((SEQ ID NO: 93))
atagcgcctgatcgcaacgcctacgatggacacgccg (-DGKa siRNA);.

SHELL1-control RNA:
(SEQ ID NO: 94)
atgcaacctgcctggcaagactccagaggactactcatccgt (-control RNA);.

SHELL4-control RNA:
(SEQ ID NO: 95)
atagcgcctgatcgcaacgcctacgatggacacgccg (-control RNA);.

In this study, five PNL24 compounds were produced. The PNL24 compounds were designed with or without RGD targeting moieties and with different RNA payloads. To differentiate the five PNL24 compounds, the names and key components of the five compounds are listed in Table 4. In the PNL24RDN and PNL24DN compounds, the DGKa siRNA and Notch-1 siRNA are carried by the same nanostructure as two different types of anti-GBM payloads. In the PNL24RC compound, the same control RNA strands are conjugated to two different components of the nanostructure and, therefore, addressed at different positions in the nanostructure.

TABLE 4

The names and key components of the five compounds produced in this study. A checkmark (✓) indicates the presence of a particular component (listed by column) in a given compound (listed by row).

| Name of Compound | Core-RGD conjugate | Shell4-DGKa siRNA | Shell1-Notch-1 siRNA | Shell4-control RNA | Shell1-control RNA |
|---|---|---|---|---|---|
| PNL24RDN | ✓ | ✓ | ✓ | | |
| PNL24RD | ✓ | ✓ | | | |
| PNL24RN | ✓ | | ✓ | | |
| PNL24DN | | ✓ | ✓ | | |
| PNL24RC | ✓ | | | ✓ | ✓ |

To attach different payloads to the nanostructures, at least two different methods were used. As a targeting moiety, the azide group at the C-terminal of the GRGDSP peptide was conjugated to the 5' hexynyl group in the Core DNA of the nanostructure with click chemistry. The aminated RNA species were covalently attached to the thiol-modified Shell DNA strands with sulfo-LC-SPDP crosslinker.

The eight "+" shaped motifs comprising PNL24 were assembled first. Each motif in a compound has one RGD-core DNA conjugate, four shell strands, and four arm DNA strands. All experiments were performed under sterile conditions. The complementary RNA was added stoichiometrically. The RGD-core DNA conjugate, shell strands, and arm strands of each motif were mixed stoichiometrically and dried at room temperature in a vacuum centrifuge. The pellet of the mixture of oligonucleotides was re-suspended in aqueous buffer with 40 mM Tris, 20 mM Acetic Acid, 2 mM EDTA, 12.5 mM Magnesium Acetate (1×TAE/Mg2+ buffer, pH=8.0) to reach 20 µM concentration. The solution was heated to 95° C., then cooled to 4° C. slowly in 24 hours and kept at 4° C. for 12 hours to stabilize the motif structure. After separately assembling the eight types of motifs, they were mixed in stoichiometric quantity and annealed from 30° C. to 22° C. over 4 hours. Then, the sample was incubated at 4° C. for 12 hours to stabilize the 2×4 grids of PNL24R-siRNA. The PNL24 compounds were dialyzed against Hank's Balanced Salt Solution (HBSS) overnight at 4° C. All five PNL24 compounds were kept in a −80° C. freezer before use.

For tumor implantation, forty (40) nu/nu mice were implanted with intracranial xenograft tumors, specifically, $1\times10^5$ U87MG cells were implanted by stereotaxic injection directly into the caudate/putamen. Mice were anesthetized by intraperitoneal injection of 3 ml/kg of a solution containing 25 mg/ml ketamine HCl, 2.5 mg/ml xylazine, and 14% ethanol in 0.85% NaCl. Surgical sites were prepared with alcohol and betadine. Animals were positioned using a stereotaxic frame with small animal adaptor, the calvarium was exposed and a 1.5 mm burr hole drilled 2 mm lateral and 1 mm anterior to the bregma. Surgery was performed with sterile tools on a sterile surface. Before the treatment phase of the experiment, the mice were housed for eight days before dosing with the compounds to allow the tumors to be established.

The compounds and control were administered intracranially with convection-enhanced delivery (CED) following the same protocol in Example 6. On each animal, 10 µl compound was dosed with CED. The concentration of each compound or control was 2.5 µM.

Animals were checked daily and euthanized immediately if moribund conditions arose. Butorphanol tartrate 5.4 mg/kg s.c. was used in the rare circumstance that animals displayed evidence of post-surgical discomfort requiring analgesics. The body weight of all mice was measured twice per week. The size of tumor was measured on days 12-14 and 23-24 after treatment. The mice will be held for Tumor Growth Delay Endpoint and complete regression/partial regression/tumor free survivor determination up to 60 days.

In this example, except for the loss of one mouse during surgery, all the mice intracranially administered with PNL24 compounds survived for at least 12 days before the first round of MRI measurement with no observable abnormalities. This observation supports the safety of PNL24 compounds.

Figure 8:
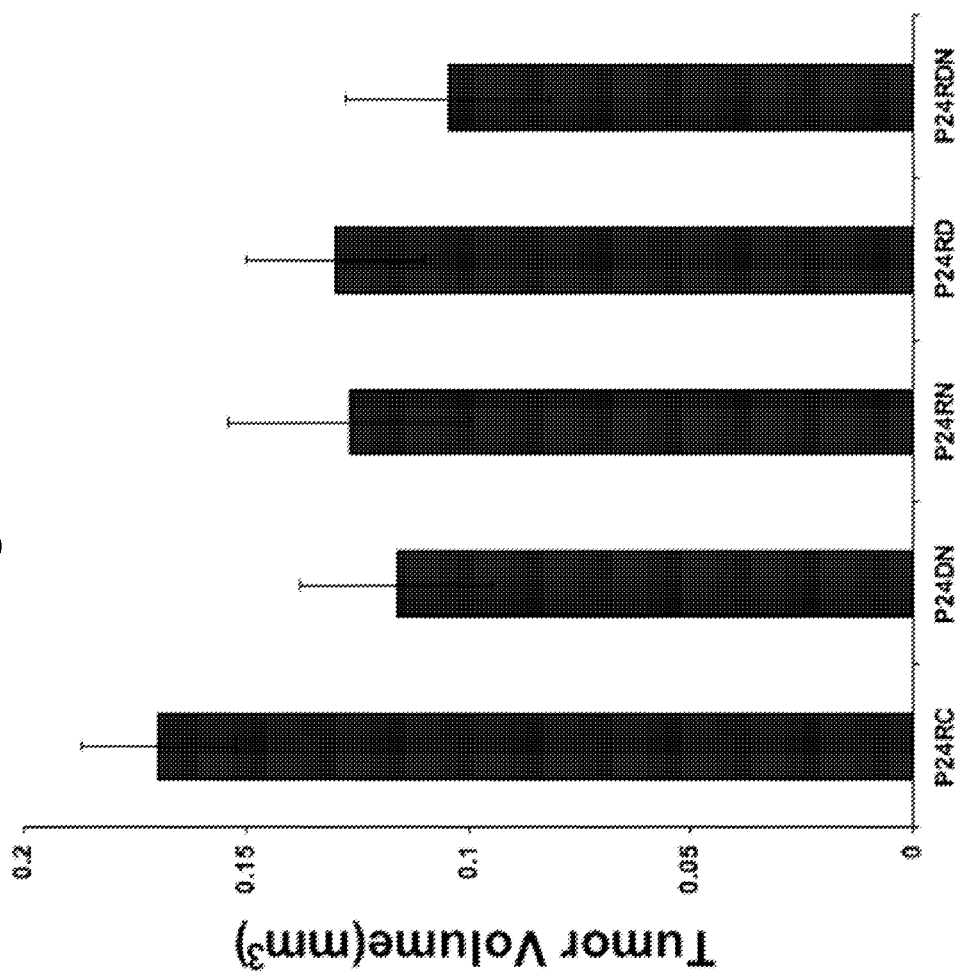
FIG. 8 is the mean tumor volume of mice on day 12-14 after treatment with nanostructure carrying anti-GBM payloads or control. The nanostructure carrying anti-GBM payloads can significantly control the growth of tumors.

FIG. 8 shows the mean tumor volume of the mice in different treatment groups on day 12-14 after dosing. (Note: The phrase "day 12-14" refers to the fact that the tumor volume of each mouse was measured exactly once at some point during the period spanning days 12-14.) The data is shown with the average tumor volume±1 standard deviation. A mouse in PNL24RD treated group was excluded from averaging due to the absence of tumor. A mouse in PNL24RN treated group was excluded because the size of tumor was too small (0.02 mm³). Data on day 12-14 after dosing shows PNL24RDN has the best efficacy among different compounds. The average tumor size of mice treated with PNL24RDN is 62% of the average tumor size of mice treated with PNL24RC control (p<0.05). Compared with the mice in PNL24RC control group, the mice treated with PNL24RD, PNL24RN, and PNL24DN also had smaller average tumor volume.

Figure 9:
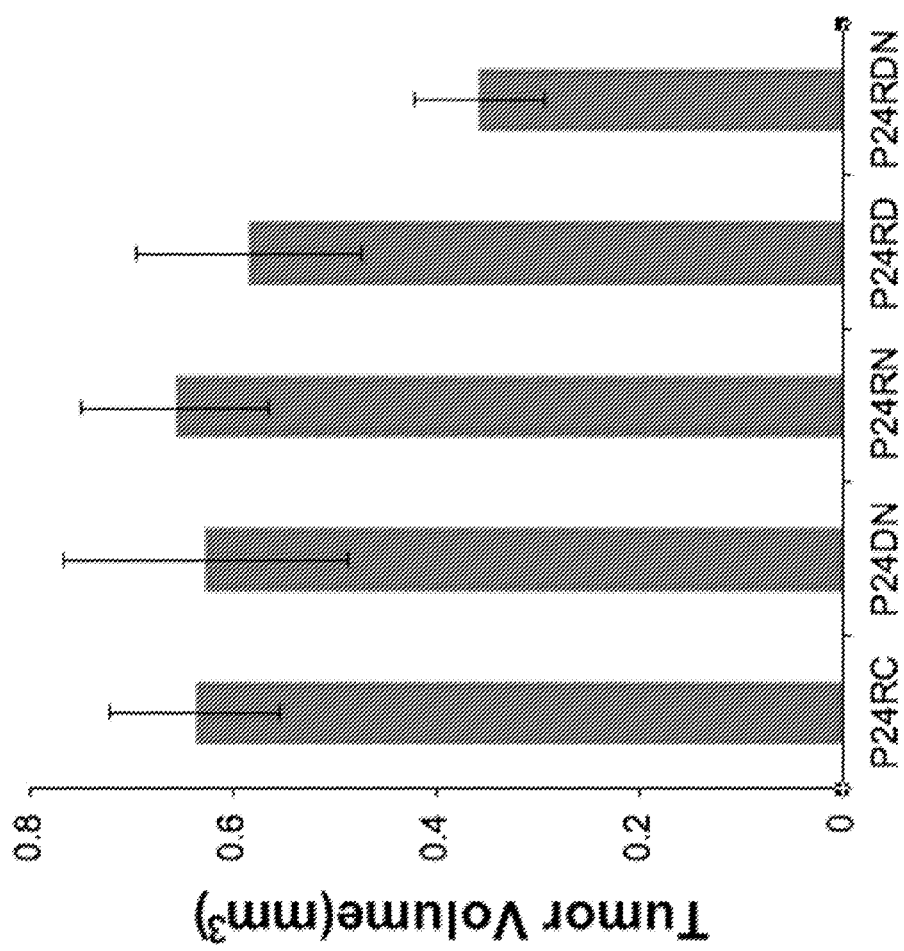
FIG. 9 is the mean tumor volume of mice on day 23-24 after treatment with nanostructure carrying anti-GBM payloads or control. The nanostructure carrying anti-GBM payloads can significantly control the growth of tumors.

FIG. 9 shows the tumor volume of the mice in different treatment groups on day 23-24 after dosing. The data is shown with the average tumor volume±1 standard deviation. Perished mice were excluded as well as mice no longer bearing tumor. Again, PNL24RDN showed best efficacy. The average tumor size of mice treated with PNL24RDN is ~56% of the average tumor size of mice treated with PNL24RC control (p<0.05)

Figure 10:
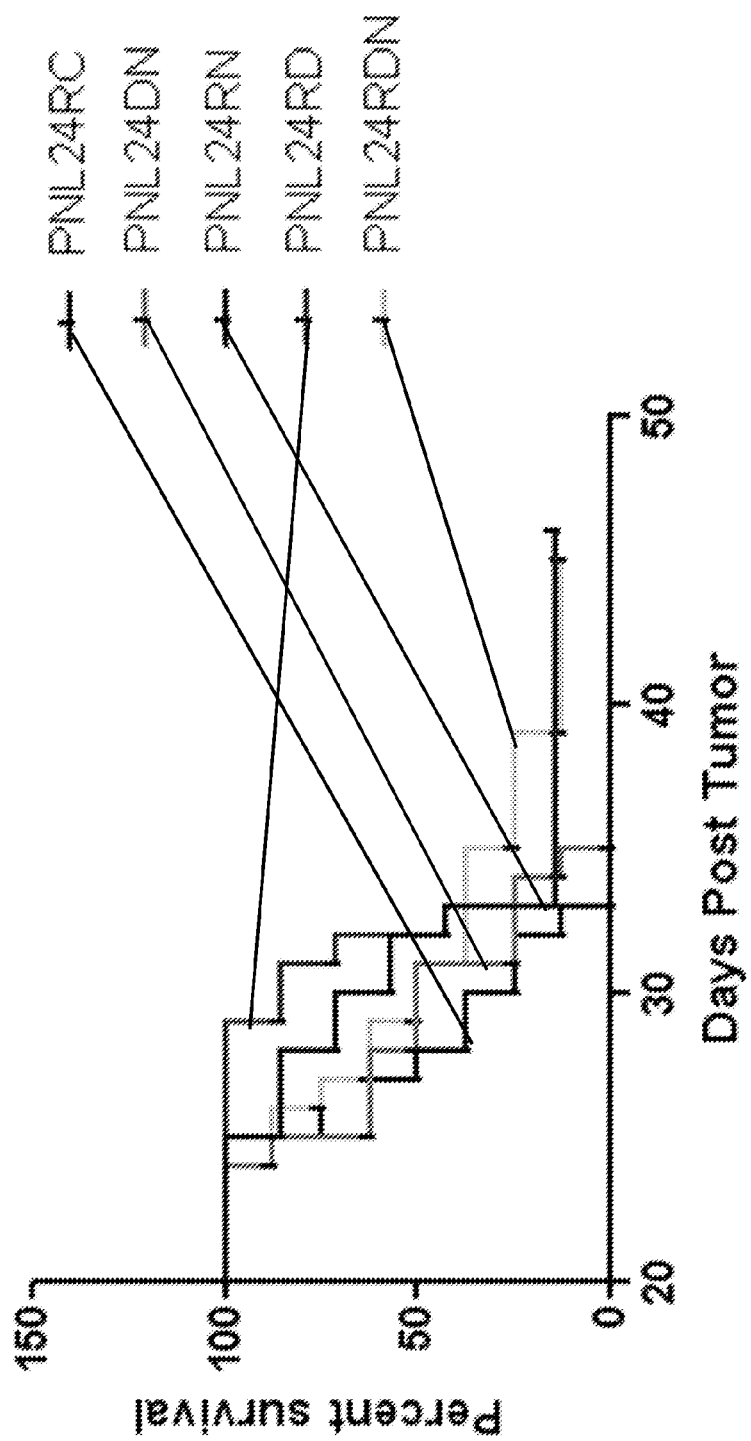
FIG. 10 shows the Kaplan-Meier survival curves of mice treated with nanostructure carrying anti-GBM payloads or control. The nanostructure carrying anti-GBM payloads can significantly extend the median survival time of treated mice.

Mouse survival data is an important factor to evaluate the anti-GBM efficacy of different PNL24 compounds. All the mice bearing detectable tumors in the first round of MRI measurement were included in the mouse survival test. FIG. 10 shows the Kaplan-Meier survival curves of all treatment and control groups. Analyzed with log-rank test, the median survival for PNL24RD group is 4.5 days longer than the median survival of PNL24RC controls (p<0.05). The median survival for other treatment groups is longer than the median survival of mice treated with the PNL24RC controls, but the difference was not statistically significant. Both the survival data and tumor size data demonstrate the anti-GBM efficacy of PNL24 compounds in vivo.

Example 8

A Nanostructure Carrying Docetaxel and a Docetaxel Sensitizer

In many cases, tumor cells can develop drug resistance to a chemo-therapy. For example, prostate cancer develops resistance to docetaxel by upregulating p38/p53/p21 signaling pathway. It has been demonstrated that p53 siRNA can be used as a sensitizer to promote the apoptosis of prostate cancer cells induced by docetaxel (Gan L, Wang J, Xu H, Yang X, Resistance to Docetaxel-Induced Apoptosis in Prostate Cancer Cells by p38/p53/p21 Signaling, The Prostate 71:1158-1166(2011).) A PNL24 compound was designed to target prostate cancer and deliver p53 siRNA and docetaxel payloads simultaneously to prostate cancer cells. Since Folate Receptor-α is overexpressed on the surface of approximately 40% of human cancers and an isoform of Folate Receptor-β is expressed on the surface of malignant cells of hematopoietic origin, folate groups were designed on the nanostructure to target the overexpressed folate receptors on prostate cancer cells. The p53 siRNA can work as a sensitizer to knockdown the expression of p53 in cancer cells and make the cancer cells more vulnerable to docetaxel.

The names and sequences of the DNA oligonucleotides used to produce PNL24 complexes are the same as the sequences in Example 1, with the following exceptions:

```
CORE-folate:
                                 (SEQ ID NO: 96)
(folate group-)aggcaccatcgtaggttttcgttgcgatcacc aacggagttttttctgccgtacaccagtgaagttttttcgatcctagc acctctggagttttcttgcc.

SHELL1-doctaxel:
                                 (SEQ ID NO: 97)
atgcaacctgcctggcaagactccagaggactactcatccgt (-docetaxel).

SHELL2-doctaxel:
                                 (SEQ ID NO: 98)
tccgactgagccctgctaggatcgacttcactggaccgttctaccga (-docetaxel).

SHELL3-doctaxel:
                                 (SEQ ID NO: 99)
(Gd-DTPA-)accggaggcttcctgtacggcagaactccgttggacga acag(-docetaxel).

SHELL4-p53 siRNA:
                                 (SEQ ID NO: 100)
atagcgcctgatcgcaacgcctacgatggacacgccg(-p53 siRNA).
```

The folate group can be conjugated to 5' aminated Core DNA with EDC. The aminated p53 siRNA can be attached to 3' thiolated Shell DNA with a sulfo-LC-SPDP crosslinker. Docetaxel can be covalently attached to thiolated Shell DNA with a SMCC crosslinker. The nanostructure can be assembled with the same method for PNL24.

Example 9

A Nanostructure Specific to GBM Cells Over Human Astrocytes In Vitro

For cancer diagnosis, it is important to differentiate cancer cells from normal cells. In this example, a TYE665 (ex. 645 nm/em. 665 nm) fluorescent dye-labeled PNL24 compound with GRGDSP peptide as targeting moiety (i.e., PNL24-R-T) was designed and produced to selectively label U87MG cancer cells over human astrocytes (HA). PNL24-R-T was annealed with the same protocol in Example 1. The names and sequences of the DNA oligonucleotides used to produce PNL24-R-T complex are the same as the sequences in Example 1, with the following exceptions (written from 5' to 3'):

```
SHELL3-TYE665:
                                 (SEQ ID NO: 101)
(TYE665-)accggaggcttcctgtacggcagaactccgttggacg aacag.

SHELL4-TYE665:
                                 (SEQ ID NO: 102)
(TYE665-)atagcgcctgatcgcaacgcctacgatggacacgccg.
```

U87MG cells and HAs were cultured separately in the wells of a 24 well plate in a $CO_2$ incubator at 37° C. in 5% $CO_2$ with 100% humidity. Each well had about $1\times10^5$ cells. U87MG cells in one well were treated with 12.5 nM PNL24-R-T for 24 hours. Untreated U87MG cells in another well were used as negative control. HA were treated with 12.5 nM PNL24-R-T in the same way with a untreated HA sample as negative control. After the PNL24-R-T treatment, the wells with cells were rinsed three times with 1 ml HBSS. Then, the cells were harvested with 0.25% trypsin for 5 min at RT and fixed with 70% ice cold ethanol. The cells were washed twice with 1 ml HBSS and resuspended in 300 ul HBSS for flow cytometry tests.

Flow cytometry was performed with a BD Biosciences FACSAria fluorescence activated cell sorter with a 633 nm excitation laser and APC (660 nm/20 nm) filter. For each sample, more than 8000 cells were interrogated. The average fluorescent intensity is listed in Table 5.

TABLE 5

The mean fluorescent intensity of U87MG and HA cell samples

|  | Mean fluorescent intensity (PNL24-R-T treated) | Mean fluorescent intensity (negative control) | Mean fluorescent intensity above background |
|---|---|---|---|
| U87MG | 721 | 161 | 560 |
| HA | 480 | 72 | 408 |

The mean fluorescent intensity of U87MG cells above background is 37% higher than the data of HA. This results demonstrate the potential application of PNL24-R-T compound as a diagnostic agent to specifically label and differentiate cancer cells. from normal human cells. For example, the nanostructures can be used to stain tissue samples obtained from surgery to label, differentiate tumor cells from normal tissue cells and show the extent of tumor invasion into normal tissue. With binding effectors specific to certain target on tumor cell, the nanostructures can even be used to differentiate the type of tumor cells and provide important information about prognosis and therapeutic plan.

Example 10

A Nanostructure as a Vaccine Against Ricin Toxin

Figure 11:
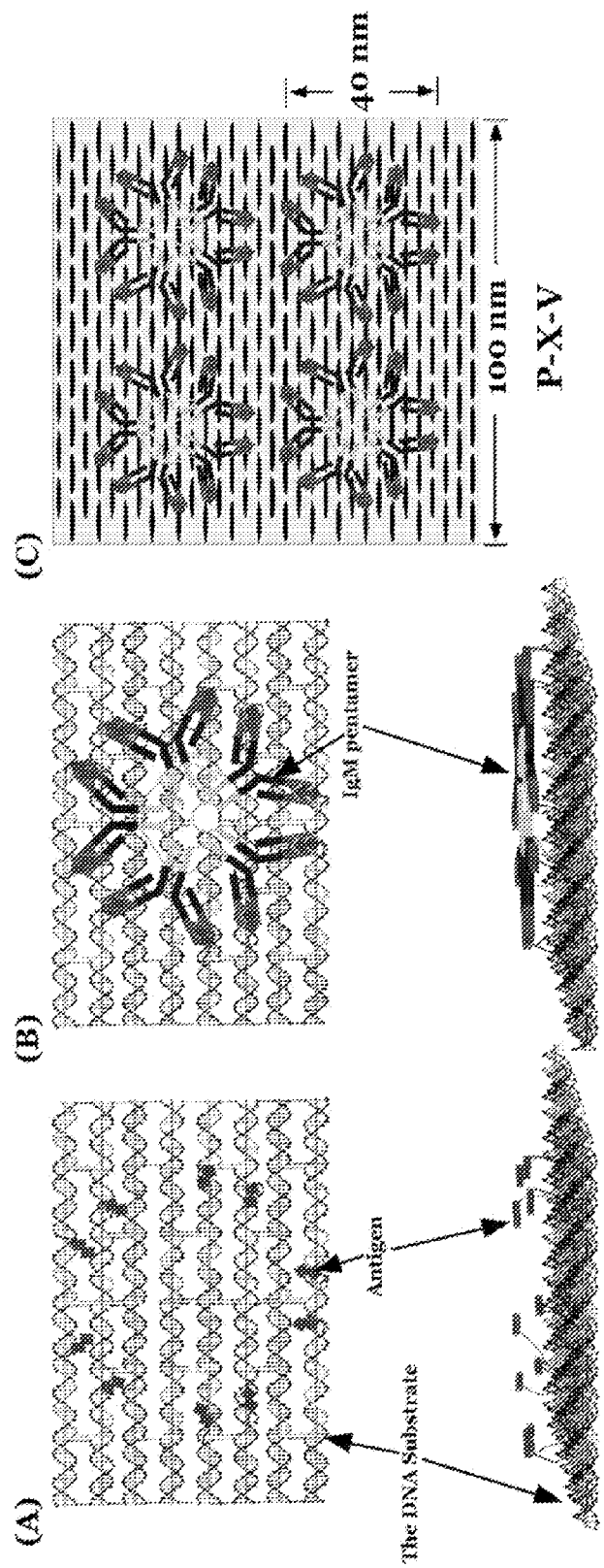
FIG. 11 is an illustration of a nanostructure-based vaccine according to one embodiment of the invention. It shows the top and side views of a pentagonal pattern of 10 (generic) antigens attached to a DNA nanostructure before (A) and after (B) binding with an IgM pentamer. (C)—Top view of a designed vaccine complex, which uses an epitope peptide from ricin A chain, to bind four IgM pentamers. Both top and bottom contain four identical binding domains for vided to give the reader a more detailed understanding of certain aspects and features of the invention.

A nanostructure, i.e., P-X-V, is designed as a vaccine against ricin toxin. In the ricin A chain, a 16mer peptide-TLARSFIICIQM (SEQ ID NO:103) has been identified as the immunodominant neutralizing epitope. The TLARSFIICIQM peptide (SEQ ID NO:104) is used as the major immunogen in the P-X-V vaccine. The TLARSFIICIQM peptide (SEQ ID NO:104) with a C-terminal azide modifier is conjugated with hexynyl modified DNA oligos to form DNA-peptide conjugates. In total, eighty (80) such DNA-peptide conjugates are self-assembled into the P-X-V vaccine complex with forty (40) of them on each surface of the nanostructure. The TLARSFIICIQM (SEQ ID NO:103) peptide molecules are aligned as four pentameric patterns as shown in FIG. 11. The pentameric patterns are optimized for the binding of IgM as well as IgG. The number of the TLARSFIICIQM peptides (SEQ ID NO:104) on each side of the nanostructure are designed to achieve optimal immunogenicity against ricin toxin, as it has been reported more than 20 antigens or haptens in one polymer can dramatically promote the efficacy to induce specific immune response. The 40 nm diameter of the pentameric patterns of the peptides was selected to have optimal accessibility to IgM, IgG, and B-cell receptors (BCRs) because IgM is usually a 40 nm pentamer with a structure similar to BCR. IgG has similar structure to a single unit of IgM. The unmethylated CpG motifs in the DNA oligos of the nanostructure are used as immunostimulators to further promote the immunogenicity of P-X-V.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

The invention claimed is:

1. A nanostructure complex comprising:
   at least one nucleic acid molecule, the linear sequences of bases of each molecule being known and artificially and deliberately assigned to cause pre-determined inter- and/or intra-molecule binding to form a pre-determined, finite, two-dimensional or three-dimensional structure,
   wherein the nanostructure complex is of a predetermined finite size, and
   wherein the nanostructure complex has—
   one or more pre-defined sequences engineered to control in vivo degradation by use of—
   one unbound helical domain, or
   two or more bound helical domains, and
   one or more pre-defined sequences engineered to bond with one or more pre-selected cell-binding moieties, the collection of which forms a pattern designed to effect cell binding, with selectivity coefficient greater than 1 and dissociation constant less than $10^{-3}$, for—
   targeting the nanostructure complex to designated target cell types, and
   causing internalization of the nanostructure complex in the target cell types,
   wherein the nanostructure complex has one or more pre-defined sequences engineered to bond with one or more pre-selected substances of interest,
   wherein the nanostructure complex is capable of delivering the substance(s) of interest to the target cell types, and
   wherein the nanostructure complex is internalized by the target cell types.

2. The nanostructure complex of claim 1, wherein the one or more pre-selected substances of interest are selected from among: therapeutic effectors, binding effectors, immunogenic effectors, immunostimulators, molecular sensors, or bioactive agents.

3. The nanostructure complex of claim 1, wherein the substance(s) is covalently bonded to the nucleic acid(s).

4. The nanostructure complex of claim 2, wherein the therapeutic effector comprises siRNA, protein, organic molecule/complex, and inorganic molecule/complex.

5. The nanostructure complex of claim 2, wherein the binding effector comprises a nucleic acid aptamer, a protein, a polypeptide, a polysaccharide, a cholesterol, or other organic/inorganic molecules and/or complexes.

6. The nanostructure complex of claim 1, wherein all of the moieties can be the same, all can be different, or some the same and others different.

7. The nanostructure complex of claim 1, wherein the identity and positioning of the nucleotide bases, nucleic acid strands, or moieties are selected to achieve one or more desired physical properties.

8. The nanostructure complex of claim 7, wherein the physical properties are selected from among size, conformation, overall charge, charge distribution, hydrophobicity, and hydrophilicity.

9. The nanostructure complex of claim 1, wherein the pre-defined portion(s) of the nucleic acid(s) are engineered to control the orientation, conformation, and/or relative positions of the pre-selected substance(s).

10. The nanostructure complex of claim 2, wherein the complex has an upper and a lower surface, and wherein the complex has at least one pre-selected substance on each of said upper and lower surfaces.

11. The nanostructure complex of claim 1, wherein the complex has a pre-defined three-dimensional structure having a longest dimension of from 2 nm to 1000 nm.

12. A method of treating a subject, comprising
administering the nanostructure complex of claim 2 to the subject in an amount sufficient to provide a treatment effect.

13. The method of claim 12, wherein the treatment effect is a prophylactic effect or a therapeutic effect.

14. The method of claim 12, wherein the nanostructure complex is administered as an immunogen, a vaccine, an immunostimulator, or as a vaccine adjuvant.

15. The method of claim 12, wherein the method is a method of treating cancer.

16. The method of claim 15, wherein the cancer is a glioma, breast cancer, prostate cancer, or lung cancer.

17. The method of claim 12, wherein at least one surface of the nanostructure complex is bound by a substance that binds red blood cells and at least one other surface is bound by a substance that binds cancer cells.

18. The method of claim 17, wherein the nanostructure complex further is bound to a cytotoxic agent on one or more of its surfaces.

19. The method of claim 14, wherein the nanostructure complex, by virtue of a highly ordered arrangement of immunogenic effectors, promotes a rapid and effective antigen-specific immunogenic response.

20. The method of claim 15, wherein the nanostructure complex comprises nucleic acid strands that are completely complementary with one another, having no unbound nucleotides at either end, which increases the circulation half-life as compared to nanostructures with one or more ends with unbound nucleotides.

21. The method of claim 15, wherein the nanostructure complex comprises two or more different substances that are specific for the same target.

22. The method of claim 15, wherein the nanostructure complex comprises a generally tubular shape defined by an outer surface and an inner surface, wherein the pre-selected substance is bound to the inner surface by disulfide linkages that are reduced upon entry of the nanostructure complex into a cell of the subject.

23. The nanostructure of claim 1, wherein the cell binding moieties are low affinity binding molecules that are specific for a tumor cell.

24. The nanostructure of claim 23, wherein the tumor cell is a glioma cell.

25. The nanostructure of claim 1, wherein the nanostructure has a half life in vivo of at least 2.7 hours.

26. A method of synthesizing a nanostructure complex of claim 1 having up to 7,000 pre-selected substances bound to the polymer(s), said method comprising
reacting amino groups of the polymer(s) of the complex with succinimidyl hemidithiodiglycolyl polyethyleneimine (SHDT-PEI) at an approximate ratio <1:5 in HEPES buffer, pH 8.0, to form a polymer-PEI;
covalently bonding the pre-selected substances to the PEI moiety of the polymer-PEI at an approximate ratio >5:1.

* * * * *

```
                         SEQUENCE LISTING

<160> NUMBER OF SEQ ID NOS: 110

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Arg Gly Asp Ser Pro
1               5

<210> SEQ ID NO 2
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
aggcaccatc gtaggttttc gttgcgatca ccaacggagt ttttctgcc gtacaccagt        60 gaagttttc gatcctagca cctctggagt ttttcttgcc                             100

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
```

```
        oligonucleotide

<400> SEQUENCE: 3
aggcaccatc gtaggtt                                                    17

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atgcaacctg cctggcaaga ctccagagga ctactcatcc gt                         42

<210> SEQ ID NO 5
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tccgactgag ccctgctagg atcgacttca ctggaccgtt ctaccga                    47

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
accggaggct tcctgtacgg cagaactccg ttggacgaac ag                         42

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atagcgcctg atcgcaacgc ctacgatgga cacgccg                               37

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Cy7

<400> SEQUENCE: 8
atgcaacctg cctggcaaga ctccagagga ctactcatcc gt                         42

<210> SEQ ID NO 9
<211> LENGTH: 47
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: 3'-Cy55

<400> SEQUENCE: 9
tccgactgag ccctgctagg atcgacttca ctggaccgtt ctaccga                    47

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-Cy7

<400> SEQUENCE: 10
atagcgcctg atcgcaacgc ctacgatgga cacgccg                               37

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gttatcggcg tgtggttgca taatac                                           26

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
caatcacgga tgagtagtgg gctcagtcgg acattc                                36

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cctcgtcggt agaacggtgg aagcctccgg tcgtgc                                36

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ttcaactgtt cgtggcgcta tattgt                                           26

<210> SEQ ID NO 15
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
caagccggcg tgtggttgca tacgac                                          26

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aagtgacgga tgagtagtgg gctcagtcgg atactg                               36

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ttgattcggt agaacggtgg aagcctccgg tttaca                               36

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gattgctgtt cgtggcgcta tgaatg                                          26

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cgaggcggcg tgtggttgca tgcacg                                          26

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttaagacgga tgagtagtgg gctcagtcgg attgta                               36

<210> SEQ ID NO 21
<211> LENGTH: 36
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 21
tcatgtcggt agaacggtgg aagcctccgg tttgct                              36

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tgtagctgtt cgtggcgcta ttacgt                                        26

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tctgacggcg tgtggttgca ttcaac                                        26

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctacaacgga tgagtagtgg gctcagtcgg aacgta                              36

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gcttgtcggt agaacggtgg aagcctccgg tgtcgt                              36

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
taacgctgtt cgtggcgcta tcattg                                        26

<210> SEQ ID NO 27
<211> LENGTH: 26
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 27
catgacggcg tgtggttgca tagcaa                                          26

<210> SEQ ID NO 28
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aacgtacgga tgagtagtgg gctcagtcgg actaac                               36

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tgctgtcggt agaacggtgg aagcctccgg ttgcag                               36

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tcattctgtt cgtggcgcta ttcaat                                          26

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ctgtgcggcg tgtggttgca ttgcac                                          26

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
atgctacgga tgagtagtgg gctcagtcgg aatgac                               36

<210> SEQ ID NO 33
<211> LENGTH: 36
<212> TYPE: DNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 33
tcagatcggt agaacggtgg aagcctccgg tgttga                              36

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
acgttctgtt cgtggcgcta tgttag                                         26

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cagcacggcg tgtggttgca tctgca                                         26

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ttagaacgga tgagtagtgg gctcagtcgg attagt                              36

<210> SEQ ID NO 37
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aatagtcggt agaacggtgg aagcctccgg ttagat                              36

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
agtacctgtt cgtggcgcta ttcaca                                         26

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 39
taactcggcg tgtggttgca ttgtat                                         26

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gtactacgga tgagtagtgg gctcagtcgg atgtga                              36

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cacagtcggt agaacggtgg aagcctccgg tgtgca                              36

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tctagctgtt cgtggcgcta ttagct                                         26

<210> SEQ ID NO 43
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
aggcaccatc gtaggtt                                                   17

<210> SEQ ID NO 44
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
atgcaacctg cctggcaaga ctccagagga ctactcatcc gt                       42

<210> SEQ ID NO 45
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 45
tccgactgag ccctgctagg atcgacttca ctggaccgtt ctaccga                    47

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
accggaggct tcctgtacgg cagaactccg ttggacgaac ag                         42

<210> SEQ ID NO 47
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
atagcgcctg atcgcaacgc ctacgatgga cacgccg                               37

<210> SEQ ID NO 48
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-DTA

<400> SEQUENCE: 48
atagcgcctg atcgcaacgc ctacgatgga cacgccg                               37

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gttatcggcg tgtggttgca taatac                                           26

<210> SEQ ID NO 50
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
caatcacgga tgagtagtgg gctcagtcgg acattc                                36

<210> SEQ ID NO 51
<211> LENGTH: 36
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 51
cctcgtcggt agaacggtgg aagcctccgg tcgtgc                                36

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ttcaactgtt cgtggcgcta tattgt                                          26

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
caagccggcg tgtggttgca tacgac                                          26

<210> SEQ ID NO 54
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
aagtgacgga tgagtagtgg gctcagtcgg atactg                               36

<210> SEQ ID NO 55
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ttgattcggt agaacggtgg aagcctccgg tttaca                               36

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gattgctgtt cgtggcgcta tgaatg                                          26

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 57
cgaggcggcg tgtggttgca tgcacg                                          26

<210> SEQ ID NO 58
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ttaagacgga tgagtagtgg gctcagtcgg attgta                               36

<210> SEQ ID NO 59
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tcatgtcggt agaacggtgg aagcctccgg tttgct                               36

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tgtagctgtt cgtggcgcta ttacgt                                          26

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tctgacggcg tgtggttgca ttcaac                                          26

<210> SEQ ID NO 62
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gcttgtcggt agaacggtgg aagcctccgg tgtcgt                               36

<210> SEQ ID NO 63
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
taacgctgtt cgtggcgcta tcattg                                         26

<210> SEQ ID NO 64
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
catgacggcg tgtggttgca tagcaa                                         26

<210> SEQ ID NO 65
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
aacgtacgga tgagtagtgg gctcagtcgg actaac                              36

<210> SEQ ID NO 66
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tgctgtcggt agaacggtgg aagcctccgg ttgcag                              36

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
tcattctgtt cgtggcgcta ttcaat                                         26

<210> SEQ ID NO 68
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ctgtgcggcg tgtggttgca ttgcac                                         26

<210> SEQ ID NO 69
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
atgctacgga tgagtagtgg gctcagtcgg aatgac                                    36

<210> SEQ ID NO 70
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tcagatcggt agaacggtgg aagcctccgg tgttga                                    36

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
acgttctgtt cgtggcgcta tgttag                                               26

<210> SEQ ID NO 72
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cagcacggcg tgtggttgca tctgca                                               26

<210> SEQ ID NO 73
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ttagaacgga tgagtagtgg gctcagtcgg attagt                                    36

<210> SEQ ID NO 74
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
aatagtcggt agaacggtgg aagcctccgg ttagat                                    36

<210> SEQ ID NO 75
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
agtacctgtt cgtggcgcta ttcaca                                          26

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
taactcggcg tgtggttgca ttgtat                                          26

<210> SEQ ID NO 77
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gtactacgga tgagtagtgg gctcagtcgg atgtga                               36

<210> SEQ ID NO 78
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cacagtcggt agaacggtgg aagcctccgg tgtgca                               36

<210> SEQ ID NO 79
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tctagctgtt cgtggcgcta ttagct                                          26

<210> SEQ ID NO 80
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Gd-DTPA

<400> SEQUENCE: 80
atgcaacctg cctggcaaga ctccagagga ctactcatcc gt                        42

<210> SEQ ID NO 81
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Gd-DTPA

<400> SEQUENCE: 81
tccgactgag ccctgctagg atcgacttca ctggaccgtt ctaccga        47

<210> SEQ ID NO 82
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Gd-DTPA

<400> SEQUENCE: 82
accggaggct tcctgtacgg cagaactccg ttggacgaac ag        42

<210> SEQ ID NO 83
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Gd-DTPA

<400> SEQUENCE: 83
atagcgcctg atcgcaacgc ctacgatgga cacgccg        37

<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
ggacgaggac gagcacuucu u        21

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
aagaagugcu cguccucguc c        21

<210> SEQ ID NO 86
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
atagcgcctg atcgcaacgc ctacgatgga cacgccg        37

<210> SEQ ID NO 87
<211> LENGTH: 21
<212> TYPE: DNA
<213> ORGANISM: Artificial Sequence -continued

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: dT

<400> SEQUENCE: 87
cgcuucacac uucccgccat t                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: dT

<400> SEQUENCE: 88
ggauugaccc uguuccuaat t                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: dT

<400> SEQUENCE: 89
uuaggaacag ggucaaucct t                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: dT

<400> SEQUENCE: 90
uucuccgaac gugucacgut t                                              21

<210> SEQ ID NO 91
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: dT

<400> SEQUENCE: 91
acgugacacg uucggagaat t                                             21

<210> SEQ ID NO 92
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
aggcaccatc gtaggttttc gttgcgatca ccaacggagt tttttctgcc gtacaccagt   60 gaagttttc gatcctagca cctctggagt ttttcttgcc                         100

<210> SEQ ID NO 93
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
atagcgcctg atcgcaacgc ctacgatgga cacgccg                            37

<210> SEQ ID NO 94
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
atgcaacctg cctggcaaga ctccagagga ctactcatcc gt                      42

<210> SEQ ID NO 95
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
atagcgcctg atcgcaacgc ctacgatgga cacgccg                            37

<210> SEQ ID NO 96
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

<223> OTHER INFORMATION: 5'-folate group

<400> SEQUENCE: 96
aggcaccatc gtaggttttc gttgcgatca ccaacggagt tttttctgcc gtacaccagt    60 gaagttttc gatcctagca cctctggagt ttttcttgcc                           100

<210> SEQ ID NO 97
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-docetaxel

<400> SEQUENCE: 97
atgcaacctg cctggcaaga ctccagagga ctactcatcc gt                       42

<210> SEQ ID NO 98
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3'-docetaxel

<400> SEQUENCE: 98
tccgactgag ccctgctagg atcgacttca ctggaccgtt ctaccga                  47

<210> SEQ ID NO 99
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Gd-DTPA
<220> FEATURE:
<223> OTHER INFORMATION: 3'-docetaxel

<400> SEQUENCE: 99
accggaggct tcctgtacgg cagaactccg ttggacgaac ag                       42

<210> SEQ ID NO 100
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
atagcgcctg atcgcaacgc ctacgatgga cacgccg                             37

<210> SEQ ID NO 101
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-TYE665

-continued

<400> SEQUENCE: 101
accggaggct tcctgtacgg cagaactccg ttggacgaac ag    42

<210> SEQ ID NO 102
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-TYE665

<400> SEQUENCE: 102
atagcgcctg atcgcaacgc ctacgatgga cacgccg    37

<210> SEQ ID NO 103
<211> LENGTH: 12
<212> TYPE: PRT
<213> ORGANISM: Ricinus communis

<400> SEQUENCE: 103

Thr Leu Ala Arg Ser Phe Ile Ile Cys Ile Gln Met
1               5                   10

<210> SEQ ID NO 104
<211> LENGTH: 12
<212> TYPE: PRT
<213> ORGANISM: Ricinus communis

<400> SEQUENCE: 104

Thr Leu Ala Arg Ser Phe Ile Ile Cys Ile Gln Met
1               5                   10

<210> SEQ ID NO 105
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ttcgttgcga tcaccaacgg agttttttct gccgtacacc agtgaagttt ttcgatccta    60
gcacctctgg agttttctt gcc    83

<210> SEQ ID NO 106
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Cy55

<400> SEQUENCE: 106
accggaggct tcctgtacgg cagaactccg ttggacgaac ag    42

<210> SEQ ID NO 107
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 107
tcgttgcgat caccaacgga gtttttctg ccgtacacca gtgaagtttt tcgatcctag      60
cacctctgga gttttcttg cc                                              82

<210> SEQ ID NO 108
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
ctacaacgga tgagtagtgg gctcagtcgg aacgta                              36

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: dT

<400> SEQUENCE: 109
uggcgggaag ugugaagcgt t                                              21

<210> SEQ ID NO 110
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
atgcaacctg cctggcaaga ctccagagga ctactcatcc gt                       42
```